US012569263B2

(12) United States Patent
Anderson et al.

(10) Patent No.: US 12,569,263 B2
(45) Date of Patent: Mar. 10, 2026

(54) SURGICAL DRILL GUIDE APPARATUS AND METHODS

(71) Applicant: INS Ortho, Inc., Providence, RI (US)

(72) Inventors: Christian N. Anderson, Nashville, TN (US); Christopher L. Ramsay, West Wareham, MA (US); Samuel Grossman, Barrington, RI (US)

(73) Assignee: INS Ortho, Inc., Providence, RI (US)

( * ) Notice: Subject to any disclaimer, the term of this patent is extended or adjusted under 35 U.S.C. 154(b) by 0 days.

(21) Appl. No.: 19/040,970

(22) Filed: Jan. 30, 2025

(65) Prior Publication Data

US 2025/0241663 A1      Jul. 31, 2025

Related U.S. Application Data

(60) Provisional application No. 63/626,751, filed on Jan. 30, 2024.

(51) Int. Cl.
| | |
|---|---|
| *A61B 17/17* | (2006.01) |
| *A61B 90/00* | (2016.01) |
| *A61B 17/00* | (2006.01) |
| *A61B 17/56* | (2006.01) |

(52) U.S. Cl.
CPC ........ *A61B 17/1764* (2013.01); *A61B 90/361* (2016.02); *A61B 2017/00424* (2013.01); *A61B 2017/564* (2013.01)

(58) Field of Classification Search
CPC ...... A61B 17/1764; A61B 2017/00424; A61B 2017/564; A61B 90/361
See application file for complete search history.

(56) References Cited

U.S. PATENT DOCUMENTS

| | | | |
|---|---|---|---|
| 5,458,602 A | 10/1995 | Goble et al. | |
| 8,690,885 B2 * | 4/2014 | Smith ................ | A61B 17/1714 606/96 |
| 11,490,791 B2 * | 11/2022 | Kielack ................. | A61B 90/50 |
| 2002/0032450 A1 | 3/2002 | Trudeau et al. | |

(Continued)

FOREIGN PATENT DOCUMENTS

WO      2023/200687 A1      10/2023

OTHER PUBLICATIONS

International Search Report and Written Opinion issued in related Application Serial No. PCT/US2025/013636 on May 8, 2025.

*Primary Examiner* — Sameh R Boles
(74) *Attorney, Agent, or Firm* — Holland & Knight LLP; Matthew C. Cox; Forrest S. Tinnin

(57) ABSTRACT

An apparatus for positioning and guiding a drill for forming a bone passage during surgery is provided. The apparatus may include a handle and a sleeve disposed on the handle. The sleeve may be configured to receive a drill. The apparatus may further include a neck disposed on the handle and a lever disposed on the neck. The neck may be movable in translation relative to the handle. The lever may be angularly movable in rotation relative to the neck. The apparatus may further include a guide arm disposed on the lever and a neck locking mechanism disposed on the handle. The neck locking mechanism configured to hold the neck in place relative to the handle passage and release the neck. The apparatus may further include a detent mechanism configured to provide a resistance against rotation of the lever.

19 Claims, 30 Drawing Sheets

(56) References Cited

U.S. PATENT DOCUMENTS

| 2018/0153564 A1* | 6/2018 | Cunningham ........ A61F 2/0811 |
| 2019/0231370 A1 | 8/2019 | Muser |
| 2020/0222066 A1 | 7/2020 | Cunningham et al. |

* cited by examiner

SURGICAL DRILL GUIDE APPARATUS AND METHODS

CROSS-REFERENCES TO RELATED APPLICATIONS

This application is a non-provisional of and claims priority to and benefit of U.S. Provisional Patent Application No. 63/626,751, filed Jan. 30, 2024, entitled "SURGICAL DRILL GUIDE APPARATUS AND METHODS," which is hereby incorporated by reference in its entirety.

STATEMENT REGARDING FEDERALLY SPONSORED RESEARCH OR DEVELOPMENT

Not Applicable.

REFERENCE TO SEQUENCE LISTING OR COMPUTER PROGRAM LISTING APPENDIX

Not Applicable.

BACKGROUND

The present disclosure relates generally to arthroscopic surgery. More particularly, the present disclosure relates to apparatuses and methods for positioning and guiding drills used to form passages in bone.

The meniscal root is the anchor point of the meniscus on the tibial surface. Various knee-related injuries require meniscal root repair. For instance, medial meniscal root tears typically involve tears at or about the meniscal root insertion on the tibial surface. Most described techniques for meniscal root repair use a guide placed into an anteromedial ("AM") portal while a camera is placed into the anterolateral ("AL") portal for viewing of the medial root insertion by the operator performing the procedure. In turn, a passage may be drilled in the tibial bone in order to implement a suture or some other implement configured to secure the meniscal root. Placing the guide in the AM portal and viewing from the Anterolateral portal makes visualization of the medial root insertion very difficult. Poor visualization can lead to poor implementation of the passage and ensuing suture, which may lead to poor restoration of the biomechanical function of the meniscus, and thus ultimate failure of the surgery. To compensate for this poor visualization, a "reverse notchplasty" (e.g., removal of the medial tibial spine) is often necessary, which creates an additional step and increased morbidity of the operation. Even after taking the additional steps of reverse notchplasty and removal of tibial spine, visualization of the root is often inadequate in order to prevent the aforementioned issues.

What is needed are improvements in apparatuses and methods for positioning and guiding drills used to form passages in tibial bone.

BRIEF SUMMARY

This Brief Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

One aspect of the present disclosure is an apparatus for positioning a drill for forming a bone passage during surgery. The apparatus may include a handle, a neck, a sleeve, a cuff, and a guide arm. The handle may include a first passage (e.g., a handle passage, a neck passage, etc.) defined therein and a second passage (e.g., a drill passage, a sleeve passage, etc.) defined therein. The sleeve may be disposed on handle (e.g., or in the second in the passage and be configured to receive a drill. The neck may be disposed on the handle (e.g., in the first passage). The neck may be disposed in or the passage and may be movable in translation relative to the handle passage. The cuff may be disposed on the neck. The guide arm may be disposed in or on the cuff and be angularly movable in rotation relative to the cuff and/or neck.

In some embodiments, the apparatus further includes a lever. The lever may be disposed on the guide arm. The lever may be configured to be rotated such that the guide arm is rotated relative to the handle. The lever may be configured to be rotated such that the guide arm is rotated within the cuff. The handle may be configured to be gripped in a hand of a user, and the lever may be configured to be rotated by a thumb of the user. In further embodiments, the lever is disposed on the neck or the cuff.

In some embodiments, the apparatus further includes a neck locking mechanism disposed on the handle. The neck locking mechanism may be configured to hold the neck in place relative to the handle and release the neck. The neck locking mechanism may include a hinge movable between a first hinge position where the neck locking mechanism holds the neck in place relative to the handle passage, and a second hinge position where the neck locking mechanism releases the neck. The hinge may be configured to be rotated by an index finger of the user.

In some embodiments, the apparatus further includes a sleeve locking mechanism. The sleeve locking mechanism may include a locking member having a through-hole configured to receive the sleeve. The locking member may be movable between an unlocked position where the sleeve is axially movable in translation relative to the through-hole and a locked position where the locking member prevents the sleeve from being moved away from a tip of the guide arm. The locking member may be urged by a biasing member towards the locked position.

In some embodiments, the apparatus further includes a detent mechanism disposed on the handle. The detent mechanism may be configured to provide resistance against the rotation of the lever. Accordingly, the detent mechanism may be configured to provide resistance against the rotation of the guide arm relative to the cuff.

In some embodiments, the guide arm is configured to be engaged with a tibial plateau of a knee via an anterolateral portal of the knee.

In some embodiments, the neck and the handle passage feature corresponding arcuate shapes.

Another aspect of the present disclosure is a method of positioning and guiding a drill for forming a bone passage during surgery on a knee. The method may include providing the aforementioned handle, neck, sleeve, guide arm, and lever. The method may further include providing the aforementioned cuff and neck locking mechanism. As discussed above, the handle may include the first passage handle passage defined therein and the second handle passage defined therein. The neck may be disposed in the handle passage. The cuff may be disposed on the neck. The sleeve may be configured to receive the aforementioned drill. The guide arm may include a tip and be disposed in or on the neck (e.g., the cuff). The method may further include advancing the guide arm through an anterolateral portal of the knee and positioning the guide arm (e.g., the tip of the guide arm) on a tibial plateau of the knee. The method may further include angularly moving the lever in rotation relative to the neck, such that the guide arm is angularly moved in rotation relative to the neck in response to the rotation of the lever. The method may further include moving the sleeve in translation relative to the handle, such that the sleeve is advanced towards the knee, as well as engaging the neck locking mechanism, such that the neck is held in place relative to the handle. In some embodiments, the method further includes viewing, via a camera, one or more images of the tibial plateau via an anteromedial portal of the knee. As suggested above, the method may further include advancing the sleeve through the drill passage and towards the knee.

In some embodiments, the method further includes providing a lever disposed on the guide arm, and rotating the lever such that the guide arm is angularly moved in rotation relative to the cuff.

In some embodiments, the method further includes drawing the handle away from the guide arm, such that the neck is moved in translation relative to the handle passage.

In some embodiments, the method further includes providing a neck locking mechanism disposed on the handle. The neck locking mechanism may include a hinge. The method may further include rotating the hinge, such that the neck locking mechanism secures the neck in place relative to the handle passage. The handle may be configured to be gripped in the hand of a user, the lever may be configured to be rotated by a thumb of the user, and the hinge may be configured to be rotated by an index finger of the user.

In some embodiments, the method further includes providing a detent mechanism. The detent mechanism may provide resistance against the rotation of the guide arm relative to the sleeve.

In some embodiments, the method further includes providing a sleeve locking mechanism disposed on the handle. The sleeve locking mechanism may include a locking member having a through-hole configured to receive the sleeve. The locking member may be moved from an unlocked position where the drill is axially movable in translation relative to the through-hole to a locked position where the locking member prevents the sleeve from being moved away from the tip. The locking member may be urged by a biasing member towards the locked position.

Numerous other objects, advantages and features of the present disclosure will be readily apparent to those of skill in the art upon a review of the following drawings and description of a preferred embodiment.

DETAILED DESCRIPTION

Figure 1:
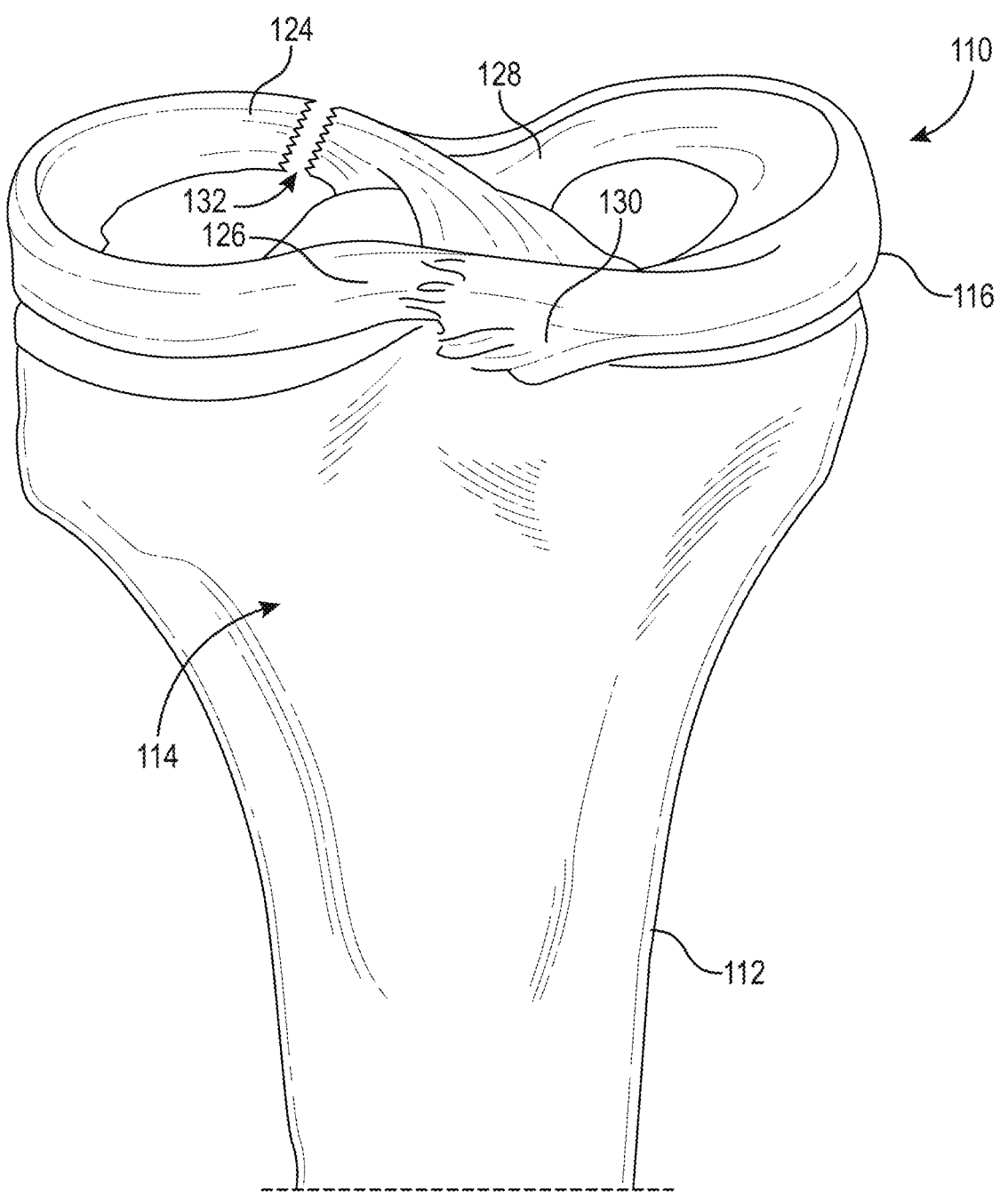
FIG. 1 is a perspective view of a portion of knee including a meniscal root tissue injury, according to some embodiments of the present disclosure.
Figures 2A, 2B:
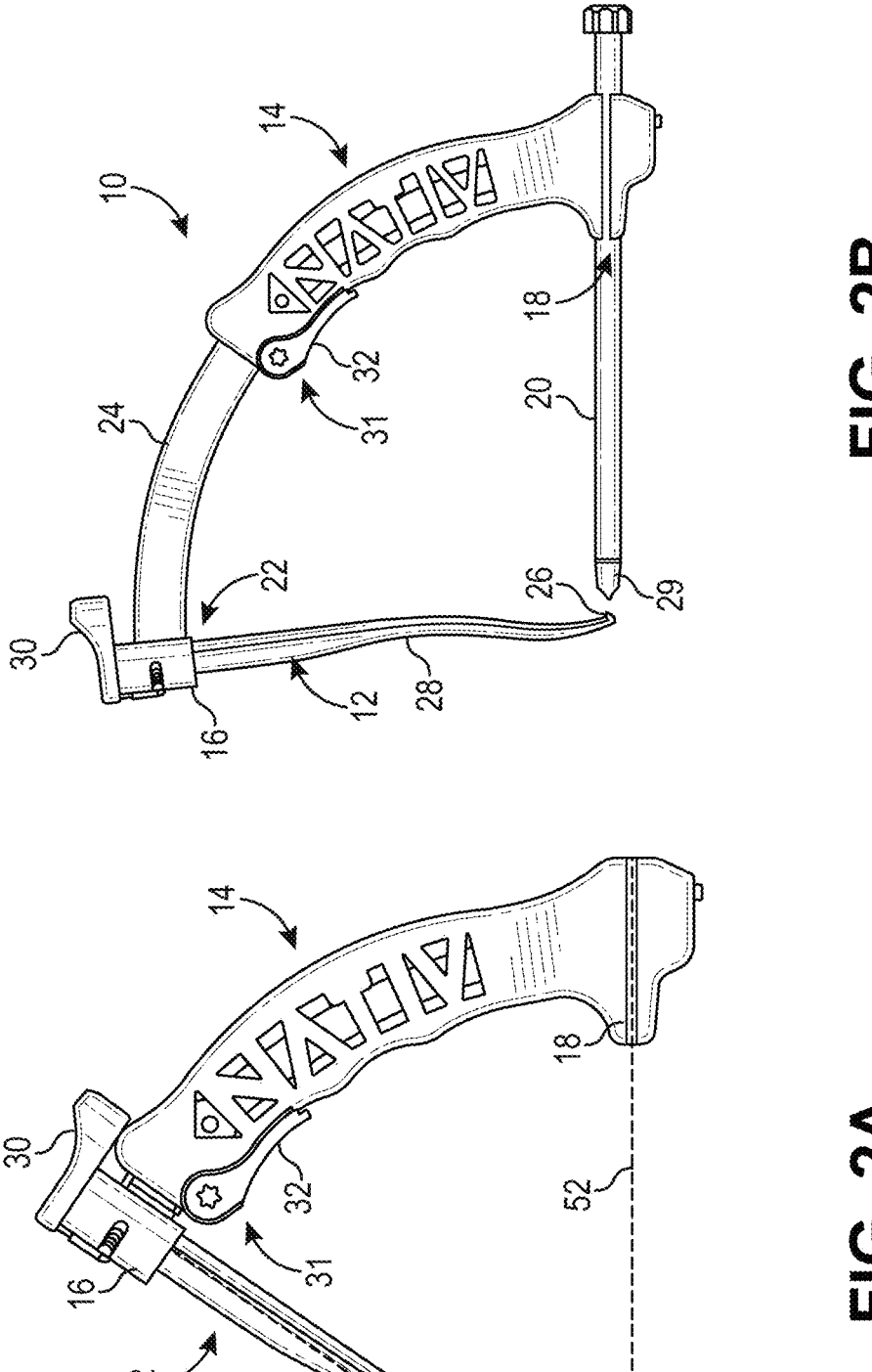
FIG. 2A is a side view of an apparatus for positioning a drill for forming a bone passage during surgery with a guide arm of the apparatus in a first guide arm position, according to some embodiments of the present disclosure.
FIG. 2B is a side view of an apparatus for positioning a drill for forming a bone passage during surgery with a guide arm of the apparatus in a second guide arm position, according to some embodiments of the present disclosure.
Figures 2C, 2D:
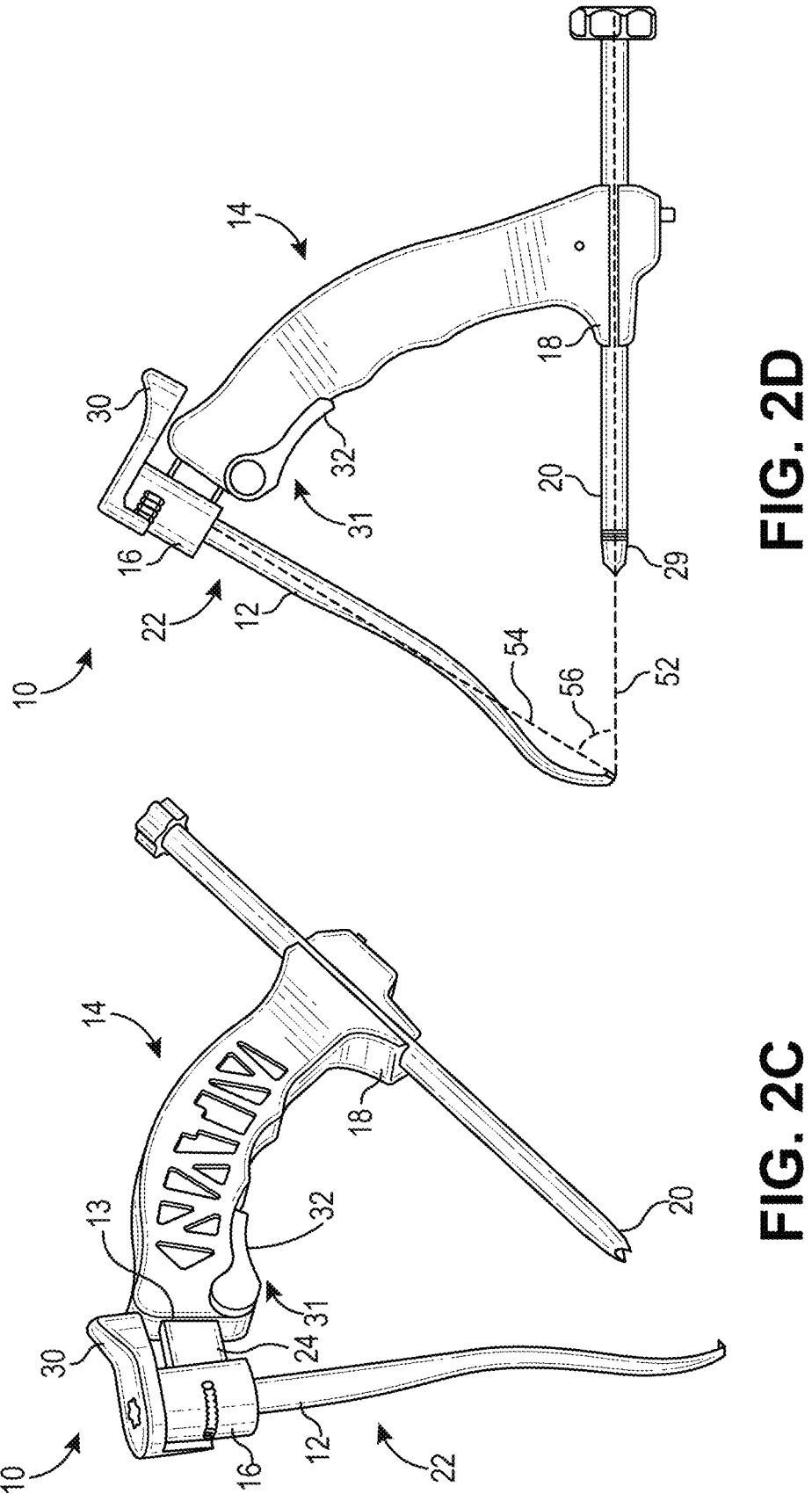
FIG. 2C is a perspective view of an apparatus for positioning a drill for forming a bone passage during surgery with a guide arm of the apparatus in a first guide arm position, according to some embodiments of the present disclosure.
FIG. 2D is a side view of an apparatus for positioning a drill for forming a bone passage during surgery with a guide arm of the apparatus in a third guide arm position, according to some embodiments of the present disclosure.
Figures 2E, 2F:
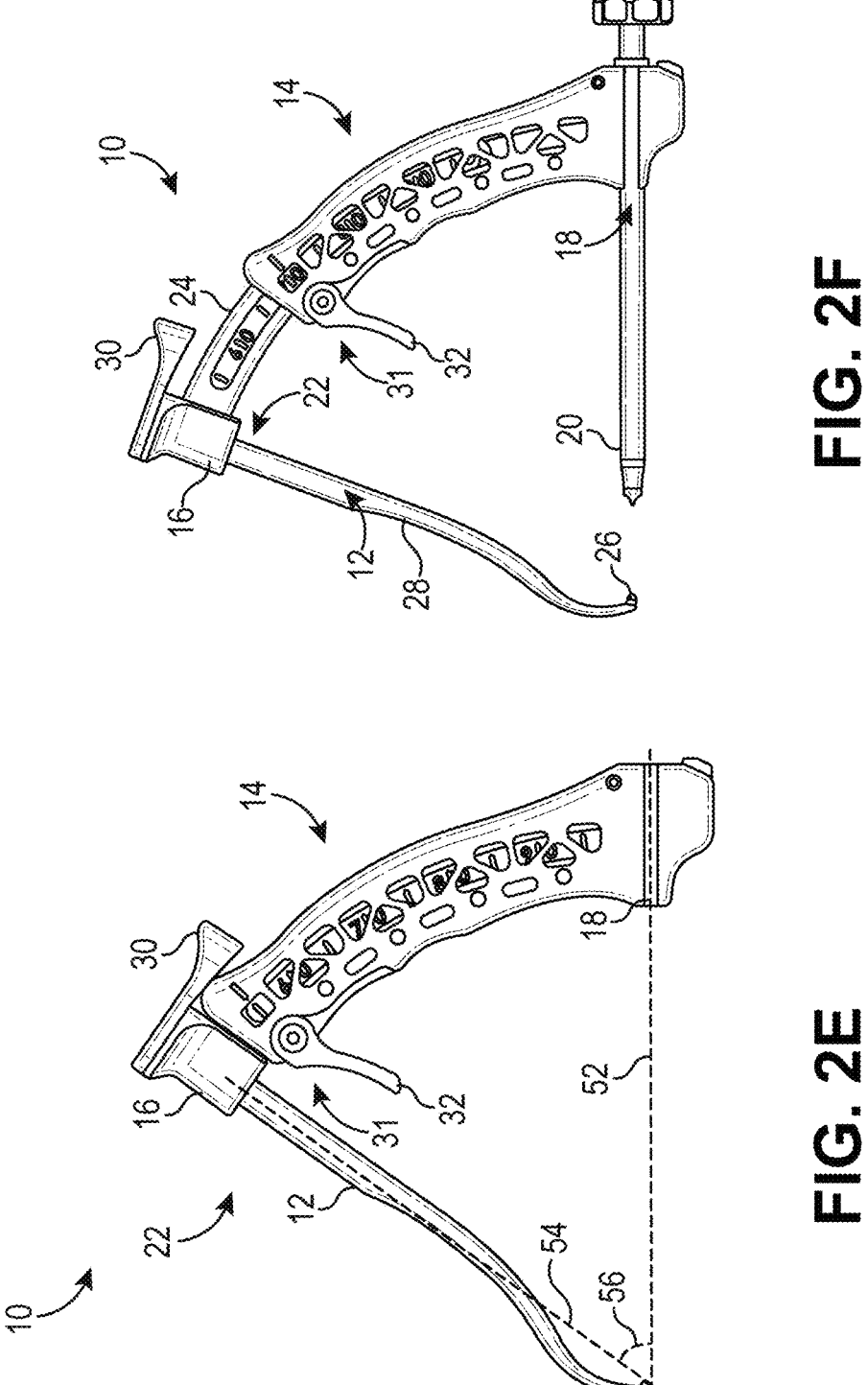
FIG. 2E is a side view of an apparatus for positioning a drill for forming a bone passage during surgery with a guide arm of the apparatus in a first guide arm position, according to further embodiments of the present disclosure.
FIG. 2F is a side view of an apparatus for positioning a drill for forming a bone passage during surgery with a guide arm of the apparatus in a second guide arm position, according to further embodiments of the present disclosure.
Figures 2G, 2H:
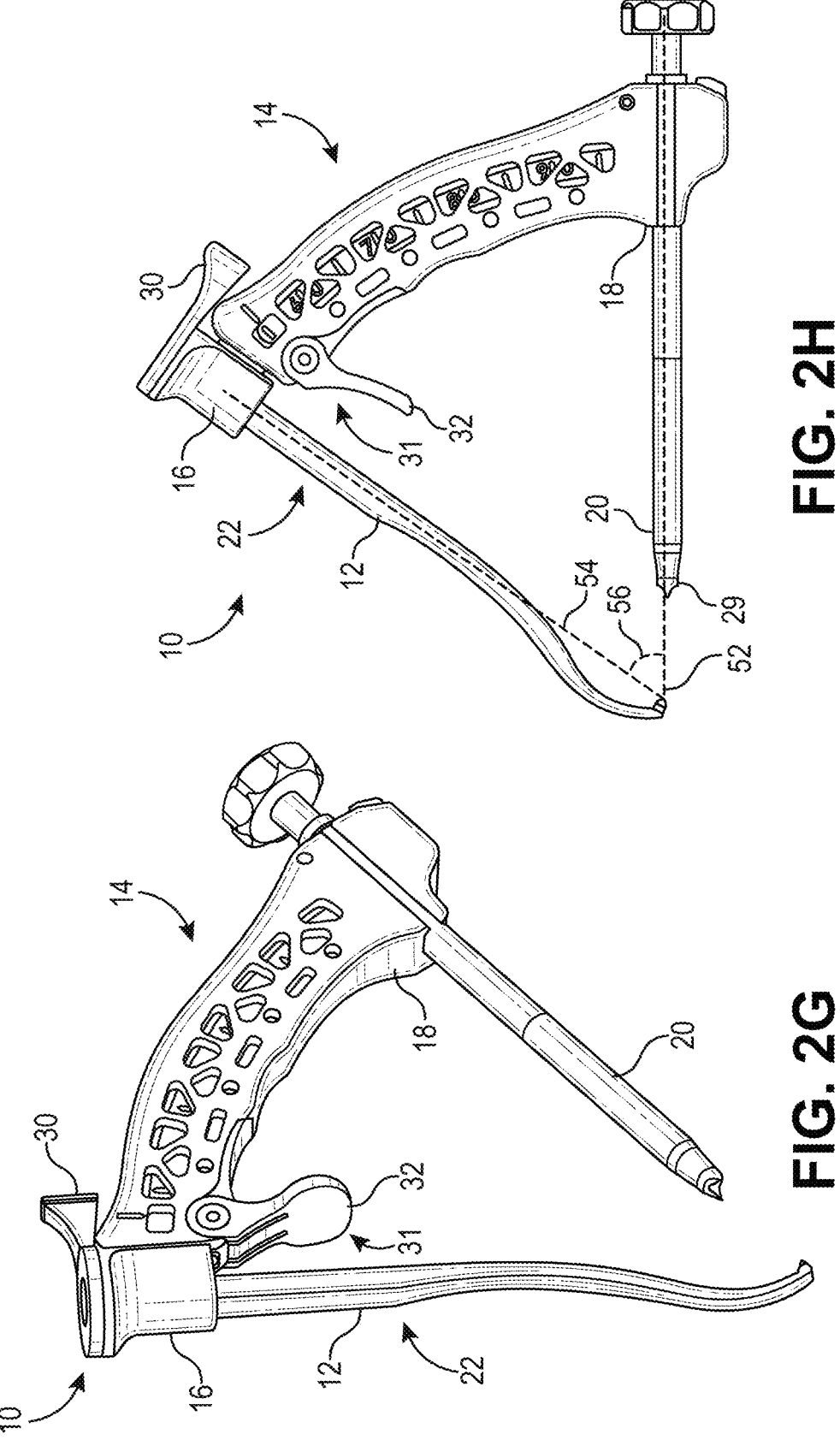
FIG. 2G is a perspective view of an apparatus for positioning a drill for forming a bone passage during surgery with a guide arm of the apparatus in a first guide arm position, according to further embodiments of the present disclosure.
FIG. 2H is a side view of an apparatus for positioning a drill for forming a bone passage during surgery with a guide arm of the apparatus in a third guide arm position, according to further embodiments of the present disclosure.
Figures 3A, 3B:
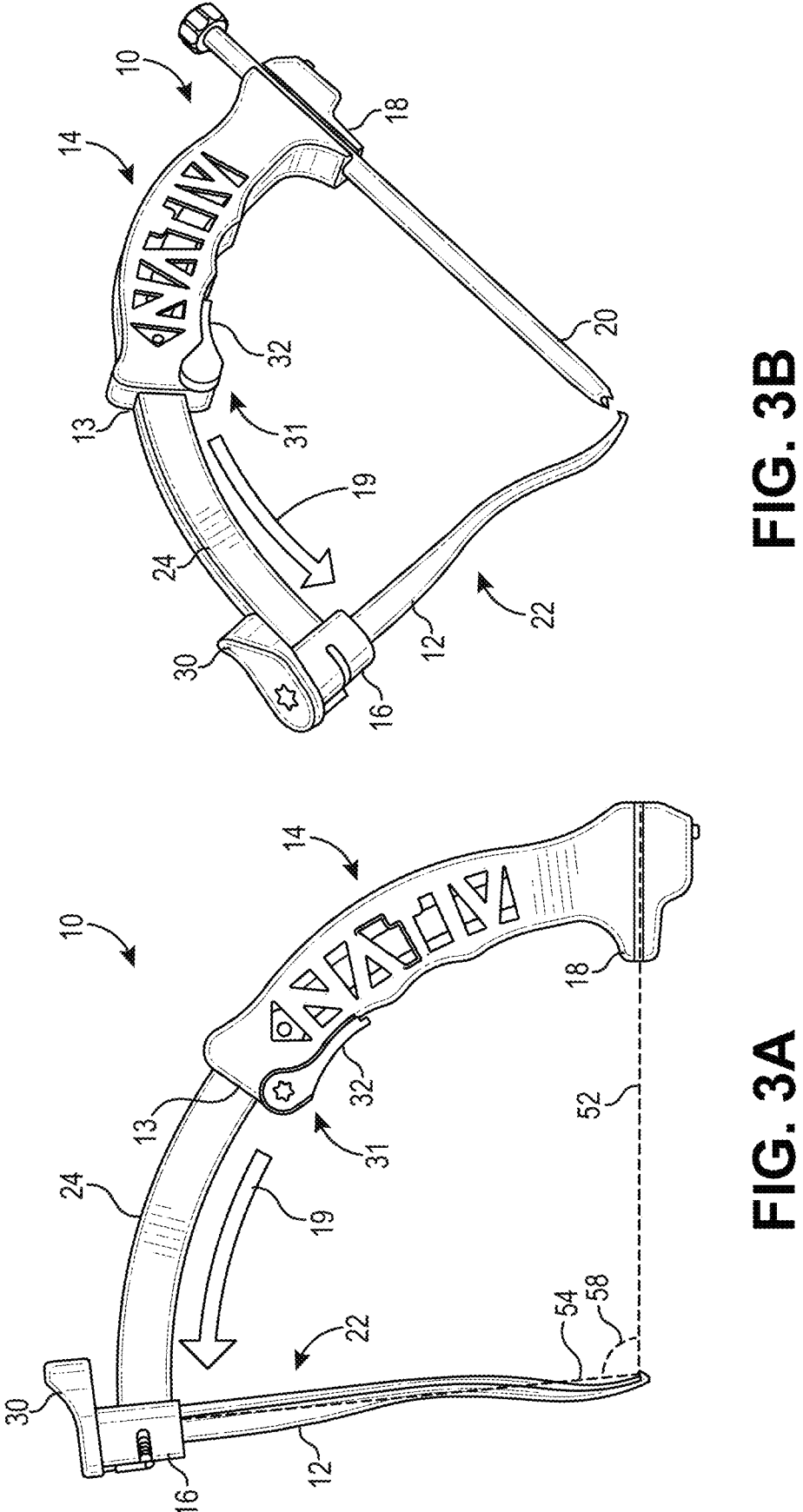
FIG. 3A is a side view of the apparatus for positioning a drill for forming a bone passage during surgery with the guide arm of the apparatus being extended towards a second guide arm position, according to further embodiments of the present disclosure.
FIG. 3B is a perspective view of an apparatus for positioning a drill for forming a bone passage during surgery with a guide arm of the apparatus being extended towards a second guide arm position, according to some embodiments of the present disclosure.
Figures 3C, 3D:
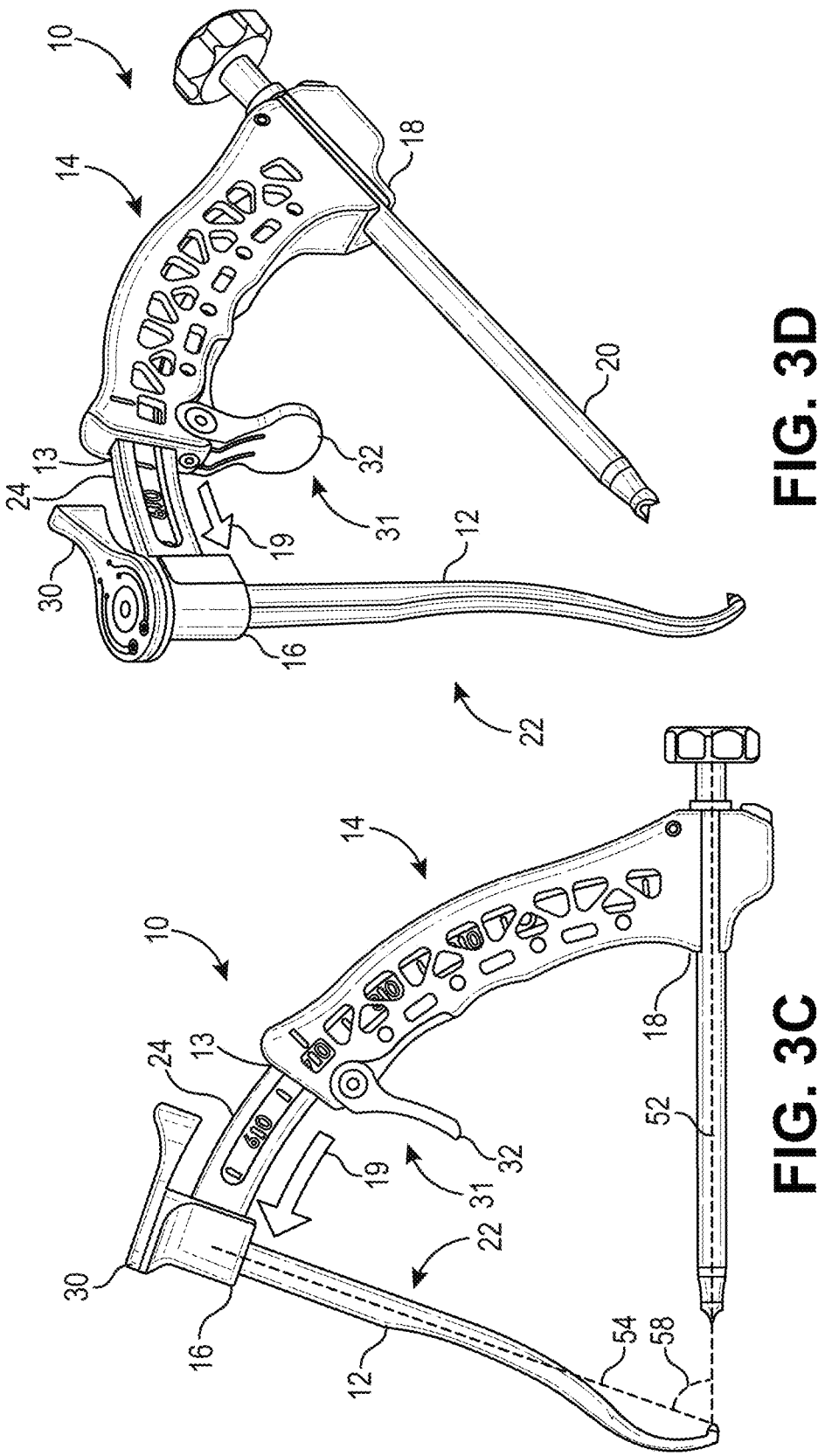
FIG. 3C is a side view of the apparatus for positioning a drill for forming a bone passage during surgery with the guide arm of the apparatus being extended towards a second guide arm position, according to further embodiments of the present disclosure.
FIG. 3D is a perspective view of an apparatus for positioning a drill for forming a bone passage during surgery with a guide arm of the apparatus being extended towards a second guide arm position, according to further embodiments of the present disclosure.

While the making and using of various embodiments of the present invention are discussed in detail below, it should be appreciated that the present invention provides many applicable inventive concepts that are embodied in a wide variety of specific contexts. The specific embodiments discussed herein are merely illustrative of specific ways to make and use the invention and do not delimit the scope of the invention. Those of ordinary skill in the art will recognize numerous equivalents to the specific apparatus and methods described herein. Such equivalents are considered to be within the scope of this invention and are covered by the claims.

In the drawings, not all reference numbers are included in each drawing, for the sake of clarity. In addition, positional terms such as "upper," "lower," "side," "top," "bottom," etc. refer to the apparatus when in the orientation shown in the drawing, or as otherwise described. A person of skill in the art will recognize that the apparatus can assume different orientations when in use.

The present disclosure provides a drill guide apparatus ("apparatus") 10 for use in surgical procedures, including but not limited to operations on the knee. For instance, the apparatus 10 may be used to position and guide drills for forming bone passages during a surgical procedure such as knee surgery. FIG. 1 shows an embodiment of a knee 110 showing the upper end of a tibia 112 including a medial meniscus 116 and a lateral meniscus 118. The medial meniscus 116 includes a posterior root 128 and an anterior root 130. The lateral meniscus 118 includes a posterior root 124 and an anterior root 126. Each root is attached to the tibia at local tissue attachment sites along the tibial plateau 114. Various types of injuries may lead to one or more root tears or injuries in the lateral or medial meniscus. An example of a root tear 132 on the lateral posterior root 124 is shown in FIG. 1.

Although various figures refer to an exemplary meniscal lateral posterior root tear injury, and the use of the apparatus 10 to address such injury, the apparatuses and methods of the present disclosure, including the apparatus 10, are applicable to many different types of injuries, including but not limited to tears and injuries in the anterior lateral meniscus and posterior lateral meniscus as well as the anterior medial meniscus, posterior medial meniscus, anterior cruciate ligament, and posterior cruciate ligament. The examples demonstrating application to a lateral posterior meniscus root tear are offered only as a non-limiting example.

Referring now to FIGS. 2A-2H, a front view of the apparatus 10 is shown, according to various embodiments of the present disclosure. As discussed in greater detail below, the apparatus 10 may include a handle 14, a neck 24 (as shown with particular reference to FIGS. 2B, 2C, and 2F), a sleeve 20, a cuff 16, and a guide arm 12 (e.g., a surgical locator probe). As shown with additional reference to FIG. 4E, the neck 24 may include a first end 24a and a second end 24b. In some embodiments, the neck 24 includes the cuff 16 defined on the first end 24a of the neck 24. In other embodiments, the cuff 16 is disposed on the neck 24.

In some embodiments, the handle 14 includes a second handle passage 18 defined therein. The second handle passage 18 may define a first longitudinal axis 52, while the guide arm 12 may define a second longitudinal axis 54. As shown with additional reference to FIG. 6G, a cuff passage 23 may be defined through the cuff 16. In further embodiments, the second longitudinal axis 54 is defined by the cuff passage 23. As shown with additional reference to FIGS. 8A-8C, the handle 14 may further include a first handle passage 15 defined therein.

As mentioned above, and as shown with particular reference to FIGS. 2B-2D and 2F-2H, the apparatus 10 may further include the sleeve 20 (e.g., a drill sleeve) disposed on the handle 14. In particular, the sleeve 20 may be disposed in the second handle passage 18. As shown with particular reference to FIGS. 2B and 2D, the sleeve 20 may be configured to receive a drill 29. Thus, the apparatus 10 may further include the drill 29. Return here In some embodiments, the neck 24 is disposed on the handle 14, and is movable in translation relative to the handle 14. In particular, the neck 24 may be disposed in the first handle passage 15 and may be movable in translation relative to the first handle passage 15. For example, and as shown with particular reference to FIG. 20, the handle 14 may include a handle opening 13 defined on an end of the first handle passage 15, through which the neck 24 may be advanced into and retracted from. As shown with additional reference to FIG. 4E, the neck 24 may include the first and second ends 24a, 24b. Thus, the first end 24a may be free of the handle passage 15, and the second end 24b may be disposed in the handle passage 15. The cuff 16 may be defined on the neck 24 (e.g., on the first end 24a). The guide arm 12 may be disposed in the cuff 16 and be angularly movable in rotation relative to the cuff 16.

As mentioned above, the neck 24 may be disposed in or on the first handle passage 15, while the sleeve 20 may be disposed in or on the second handle passage 18. Accordingly, depending on the implementation, the first handle passage 15 may be considered a "handle passage" or "neck passage," while the second handle passage 18 may be considered a "drill passage" or a "sleeve passage."

As suggested above, in some embodiments, the apparatus 10 is an apparatus for positioning the sleeve 20 for forming a bone passage during surgery. The sleeve 20 may be configured to receive and guide the drill 29 therethrough. The apparatus 10 may be used for repairing a meniscus root tear in a knee, such as the root tear 132 of the knee 110 depicted with reference to FIG. 1. Accordingly, the apparatus 10 may be configured to position and guide the drill 29 via the sleeve 20 for forming bone passages through a bone, such as the tibia 112 depicted with reference to FIG. 1, during a surgical procedure. In this sense, the apparatus 10 may be configured to provide the necessary structures and/or support for implementation of a suture or some other suitable construct for repairing the knee.

As mentioned above, the apparatus 10 may include the handle 14, the neck 24, the cuff 16, and the guide arm 12. As discussed in greater detail below with reference to FIG. 11A, the guide arm 12 (the tip 26, specifically) may be configured to be engaged with the tibial plateau 114 of the knee 110 via an anterolateral portal 138 of the knee 110 (depicted with reference to FIG. 11A). Accordingly, the guide arm 12 may be advanced into the anterolateral portal 138, thus allowing a separate camera 50 to capture or view one or more images of the tibial plateau 114 via an anteromedial portal 136 of the knee 110 (depicted with reference to FIG. 11A). In this sense, by configuring the guide arm 12 to be advanced into the anterolateral portal 138, the camera 50 may then have a clear path (via the anteromedial portal 136) to view a meniscal root (e.g., the posterior root 124 and/or the anterior root 126 depicted with reference to FIG. 1) during a surgical procedure. As depicted in greater detail with reference to FIGS. 4A-4D, the guide arm 12 and the neck 24 may be considered components of a guide arm assembly 22.

Figure 10:
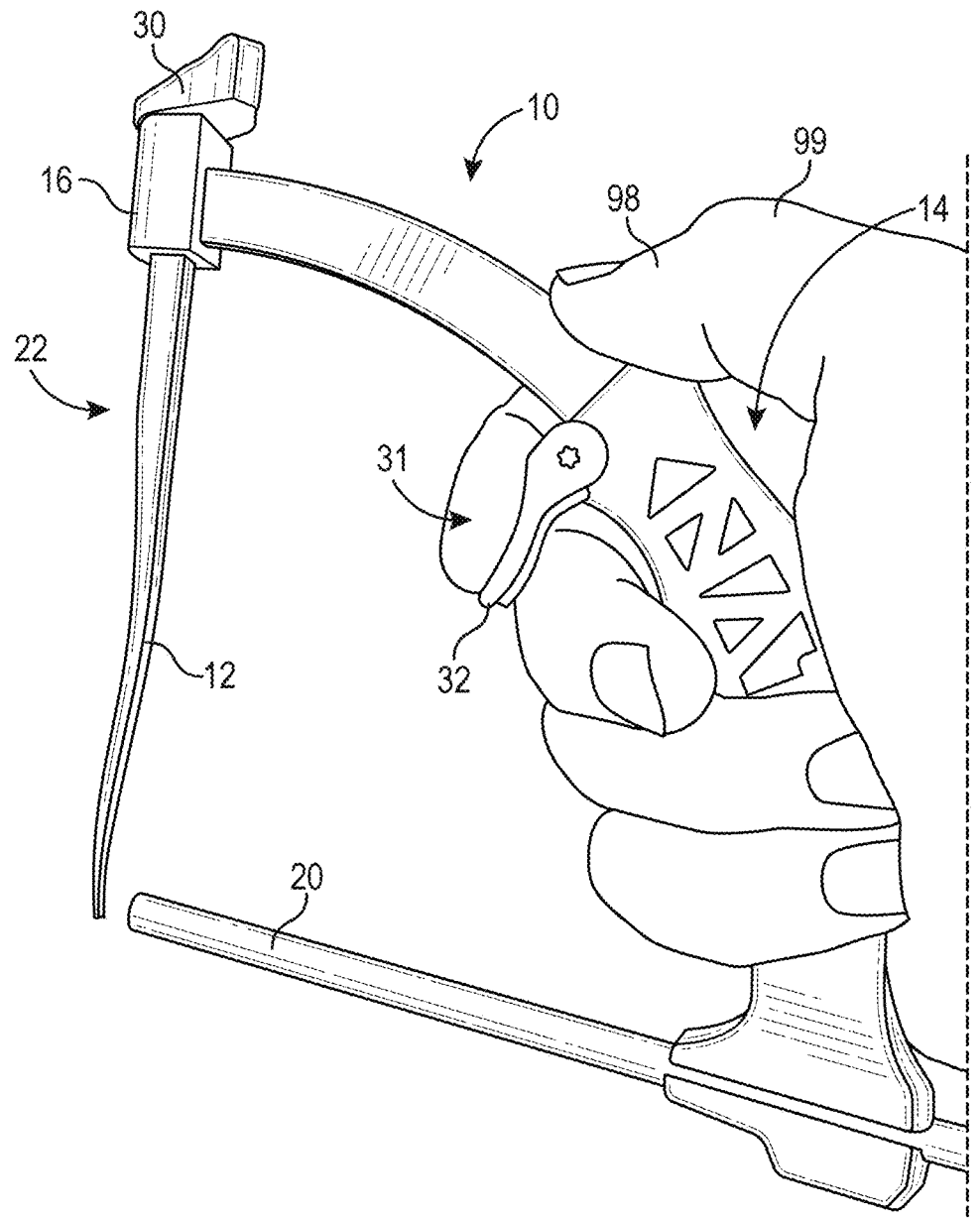
FIG. 10 is a perspective view of an apparatus for positioning a drill for forming a bone passage during surgery being held in a hand of a user, according to some embodiments of the present disclosure.

As mentioned above, the apparatus 10 may include the handle 14, which may include the first handle passage 15 and the second handle passage 18 each defined therein. As depicted with reference to FIGS. 8A-8C, the second handle passage 18 may be configured to receive the sleeve 20. As shown with reference to FIG. 10, the handle 14 may be gripped in a hand 99 of a user (e.g., an operator, doctor, surgeon, etc.) in order to perform the methods discussed herein. For instance, the handle 14 may feature a series of grooves suitable for facilitating the user gripping the handle 14.

Referring now to FIGS. 3A-3D, the apparatus 10 is shown being extended, according to various embodiments of the present disclosure. For instance, the guide arm assembly 22 may be translated relative to the handle 14. As discussed in greater detail below with reference to FIGS. 4A-4D, the guide arm assembly 22 may include the neck 24, which may be disposed within the first handle passage 15 and may be arcuately movable in translation relative to the first handle passage 15. For instance, the neck 24 may be inserted within a handle opening 13 formed on a first end of the handle 14. Accordingly, the neck 24 may be a telescoping neck. Because the handle 14 and the first handle passage 15 may be provided in an arcuate configuration, and the neck 24 may be provided in a corresponding arcuate configuration, the neck 24 may be further considered as being axially movable in translation relative to the first handle passage 15. Thus, the guide arm assembly 22 may be translated relative to the handle 14 along a path 19.

Referring now to FIGS. 4A-4E, the guide arm assembly 22 is shown, according to various embodiments of the present disclosure. As mentioned above, the guide arm assembly 22 may include the guide arm 12 and the neck 24. In some embodiments, and as shown with particular reference to FIGS. 4A and 4C, the guide arm assembly 22 further includes the cuff 16 of the neck 24. The cuff 16 may be defined on the neck 24 and may be configured to mechanically fix the guide arm 12 relative to the neck 24. As shown with particular reference to FIGS. 4B and 4D, the guide arm 12 may be provided in any configuration (e.g., length, curvature, etc.) appropriate for navigating the anterolateral portal 138.

As suggested above, the cuff 16 and the neck 24 may be formed as a single component. For example, the cuff 16 may be integrally formed on a first end of the neck 24 opposite a second end of the neck 24 that is inserted within the handle opening 13. In this sense, the cuff 16 may be permanently formed and affixed to the neck 24 (e.g., the cuff 16 may not be slidable or movable relative to the neck 24). In other embodiments, the cuff 16 is secured to the neck 24 via an adhesive or some other suitable mechanical fixation means. As mentioned above, the cuff 16 may include the cuff passage 23. The cuff passage 23 may be a longitudinal channel extending through the cuff 16, which may be configured to receive a portion of the guide arm 12. Accordingly, the guide arm 12 may be disposed in the cuff 16 and be angularly rotatable relative to the cuff 16 (and, thus, the handle 14).

Figure 4B:
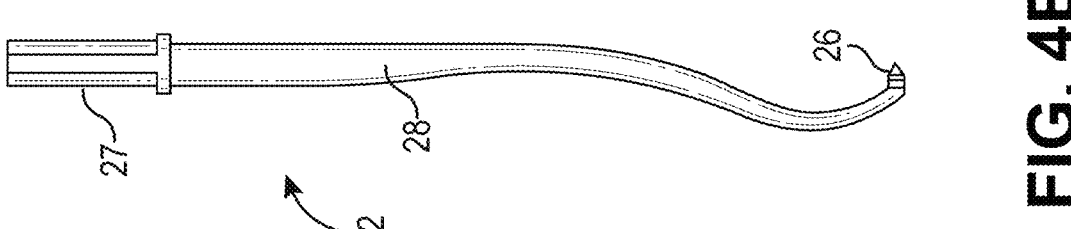
FIG. 4B is a side view of a guide arm for an apparatus for positioning a drill for forming a bone passage during surgery, according to some embodiments of the present disclosure.
Figure 4A:
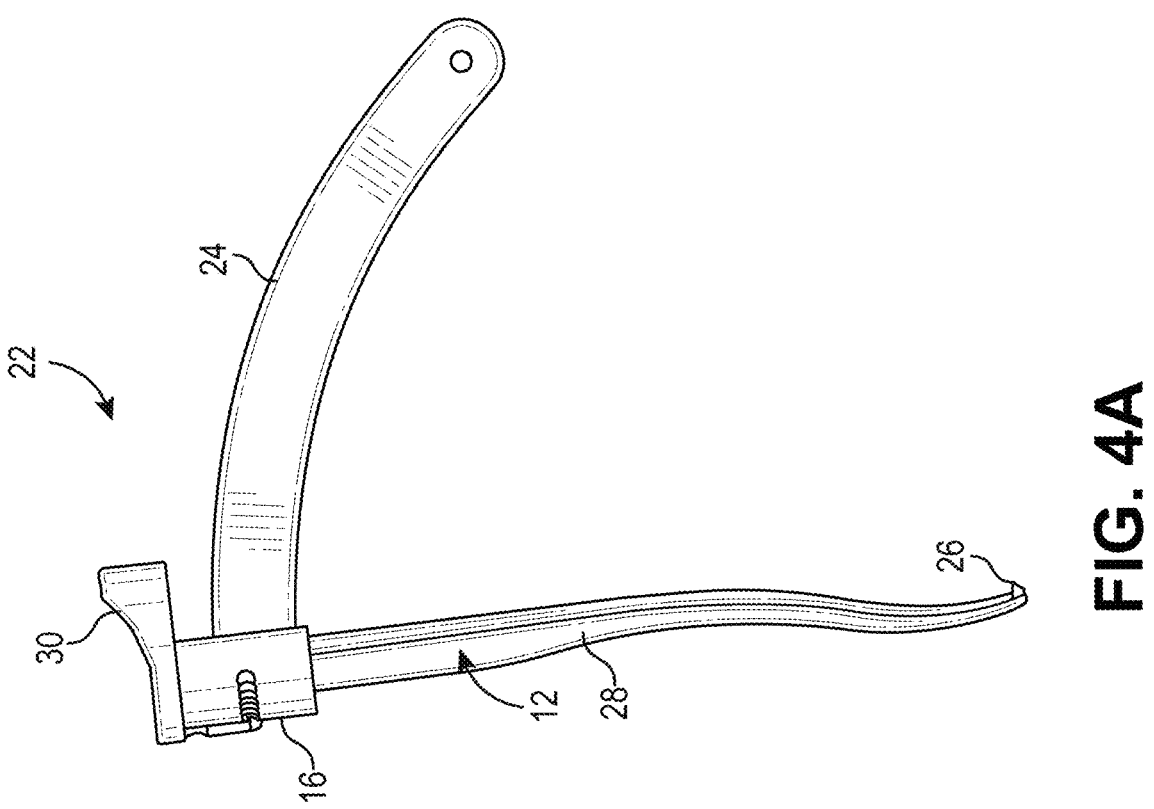
FIG. 4A is a side view of a guide arm assembly of an apparatus for positioning a drill for forming a bone passage during surgery, according to some embodiments of the present disclosure.
Figure 4D:
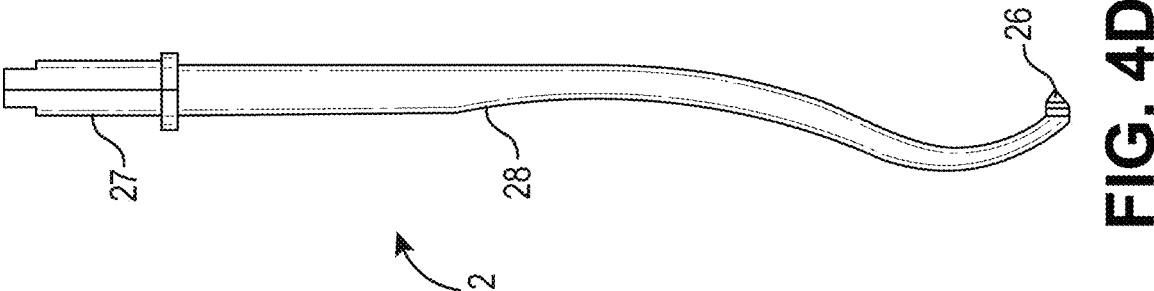
FIG. 4D is a side view of a guide arm for an apparatus for positioning a drill for forming a bone passage during surgery, according to further embodiments of the present disclosure.
Figure 4C:
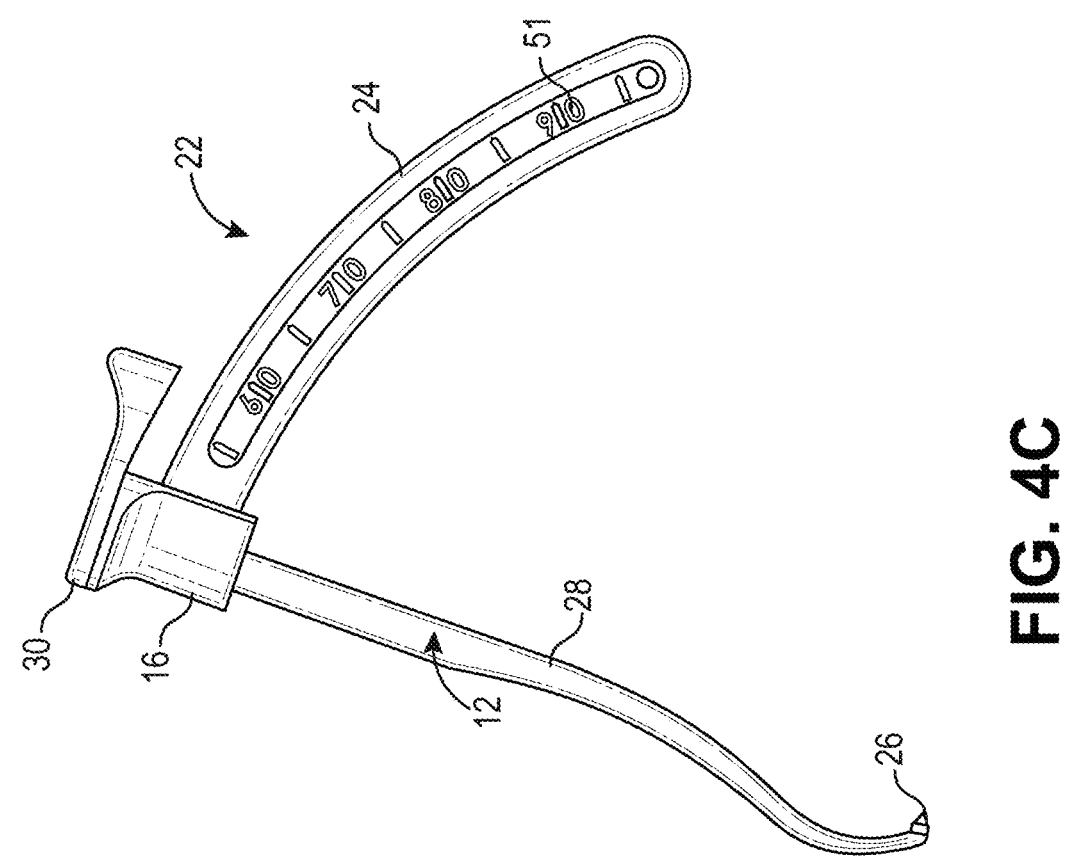
FIG. 4C is a side view of a guide arm assembly of an apparatus for positioning a drill for forming a bone passage during surgery, according to further embodiments of the present disclosure.
Figure 4E:
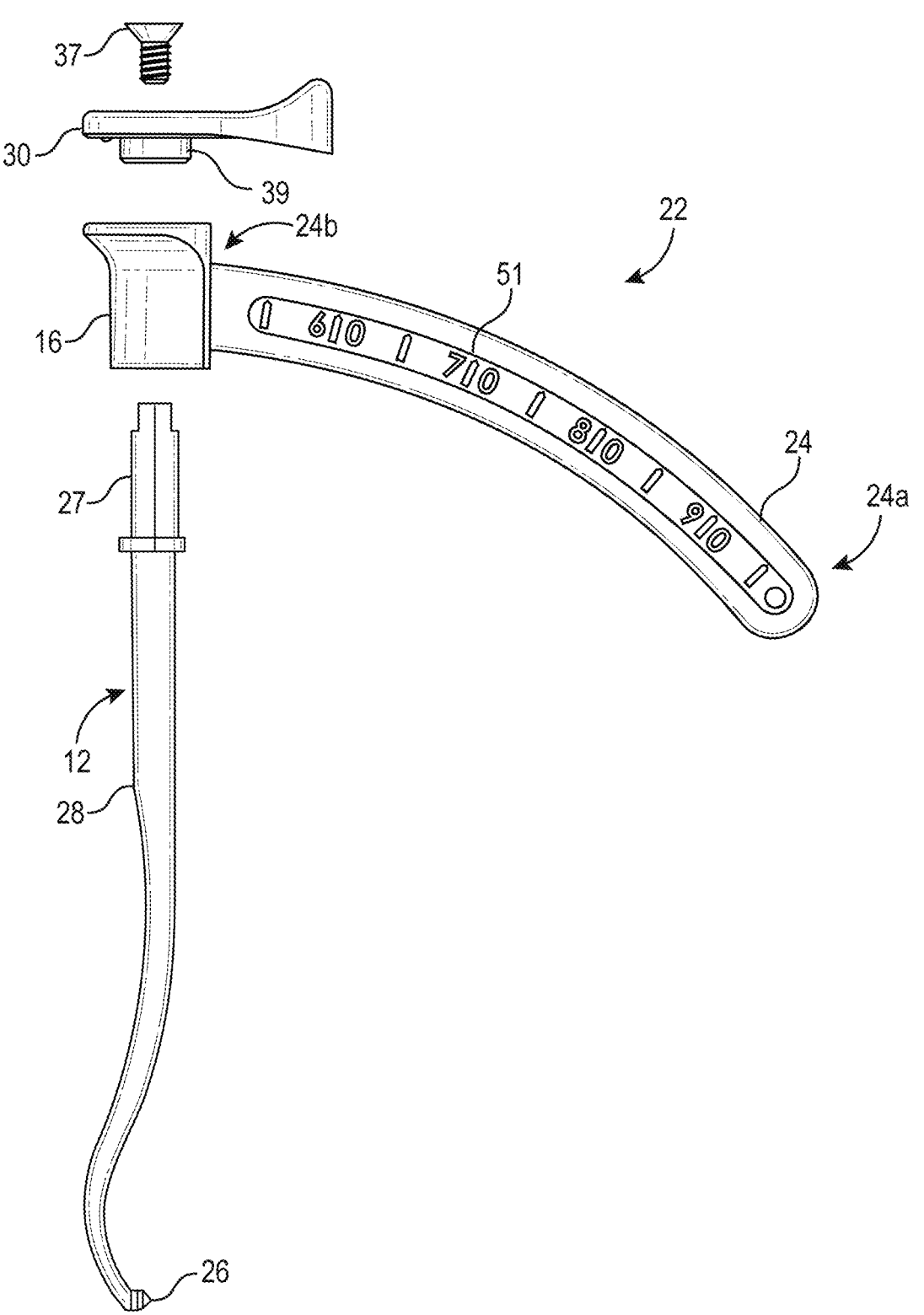
FIG. 4E is an exploded view of a guide arm assembly of an apparatus for positioning a drill for forming a bone passage during surgery, according to further embodiments of the present disclosure.

In some embodiments, and as shown with particular reference to FIGS. 4B, 4D, and 4E, the guide arm 12 includes a tip 26 on a distal end of the guide arm 12, a key 27 on a proximal end of the guide arm 12 opposite the tip 26, and guide arm curvature 28 spanning between the tip 26 and the key 27. As depicted with reference to FIG. 11A, when the guide arm 12 is advanced through the anterolateral portal 138 of the knee 110, the tip 26 may be engaged with the tibial plateau 114 of the knee 110. In order to be advanced through the anterolateral portal 138 of the knee 110, the guide arm curvature 28 may feature "biophasic" curvature, which may allow the guide arm 12 to enter the anterolateral portal 138 and contour over the tibial spine (on the tibial plateau) such that the tip 26 can be placed in contact with the meniscal root insertion (e.g., the posterior root 124 and/or the anterior root 126 depicted with reference to FIG. 1). Thus, the tip 26 may grip the tibial plateau 114 while the apparatus 10 is maneuvered as discussed herein to position the sleeve 20 in position for forming a bone passage in the knee 110 (via the drill 29 passed therethrough) during surgery.

In some embodiments, and as shown with particular reference to FIGS. 4C and 4E, the neck 24 features indicia 51. For example, the indicia 51 may be numeric etchings. The indicia 51 may provide a visual indication of the angular translation of the guide arm 12 and the sleeve 20.

As discussed in greater detail below, the apparatus 10 may further include a lever 30. In some embodiments, the lever 30 is disposed on the neck 24. In other embodiments, the lever 30 is disposed on the guide arm 12. In other words, the guide arm 12 may be disposed on the lever 30.

In some embodiments, the lever 30 is angularly movable relative to the handle 14. For example, the lever 30 may be configured to be rotated such that the guide arm 12 is rotated within the cuff 16. In this sense, the guide arm assembly 22 may further include the lever 30.

In some embodiments, and as shown with particular reference to FIG. 4E, the guide arm assembly 22 may be assembled via a mechanical fixation between the lever 30 and the guide arm 12. For example, the guide arm assembly 22 may further include a fastener 37 (e.g., a screw). As shown with additional reference to FIG. 6G, the key 27 of the guide arm 12 may feature threading 29 corresponding to the fastener 37.

Figure 6B:
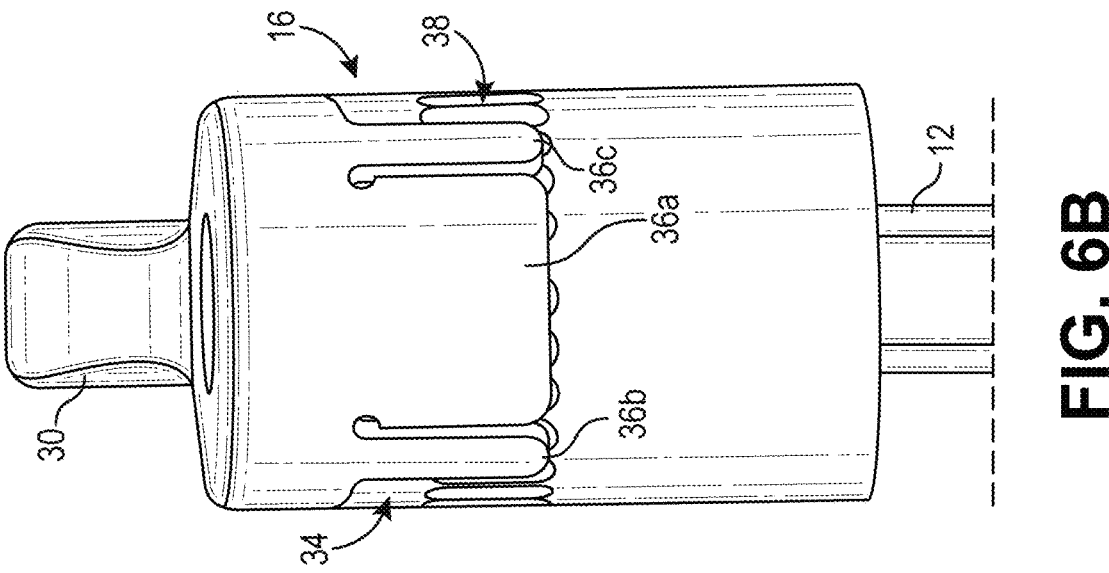
FIG. 6B is a detailed front perspective view of a lever for rotating a guide arm of an apparatus for positioning a drill for forming a bone passage during surgery, according to some embodiments of the present disclosure.
Figure 6A:
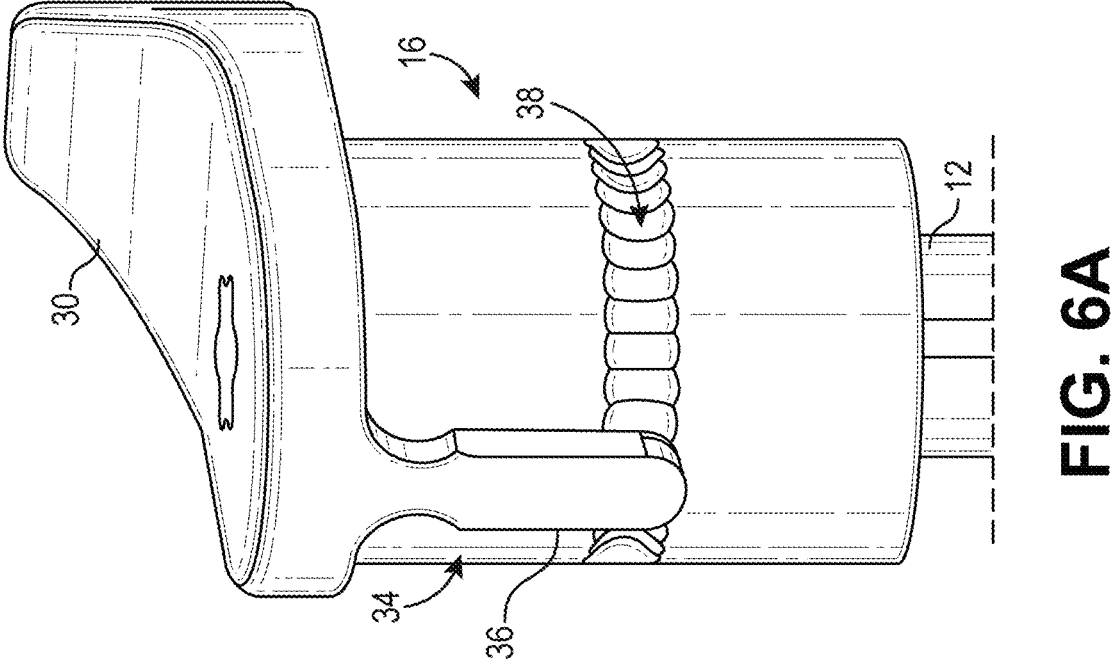
FIG. 6A is a side perspective view of a lever for rotating a guide arm of an apparatus for positioning a drill for forming a bone passage during surgery, according to some embodiments of the present disclosure.
Figures 6C, 6D:
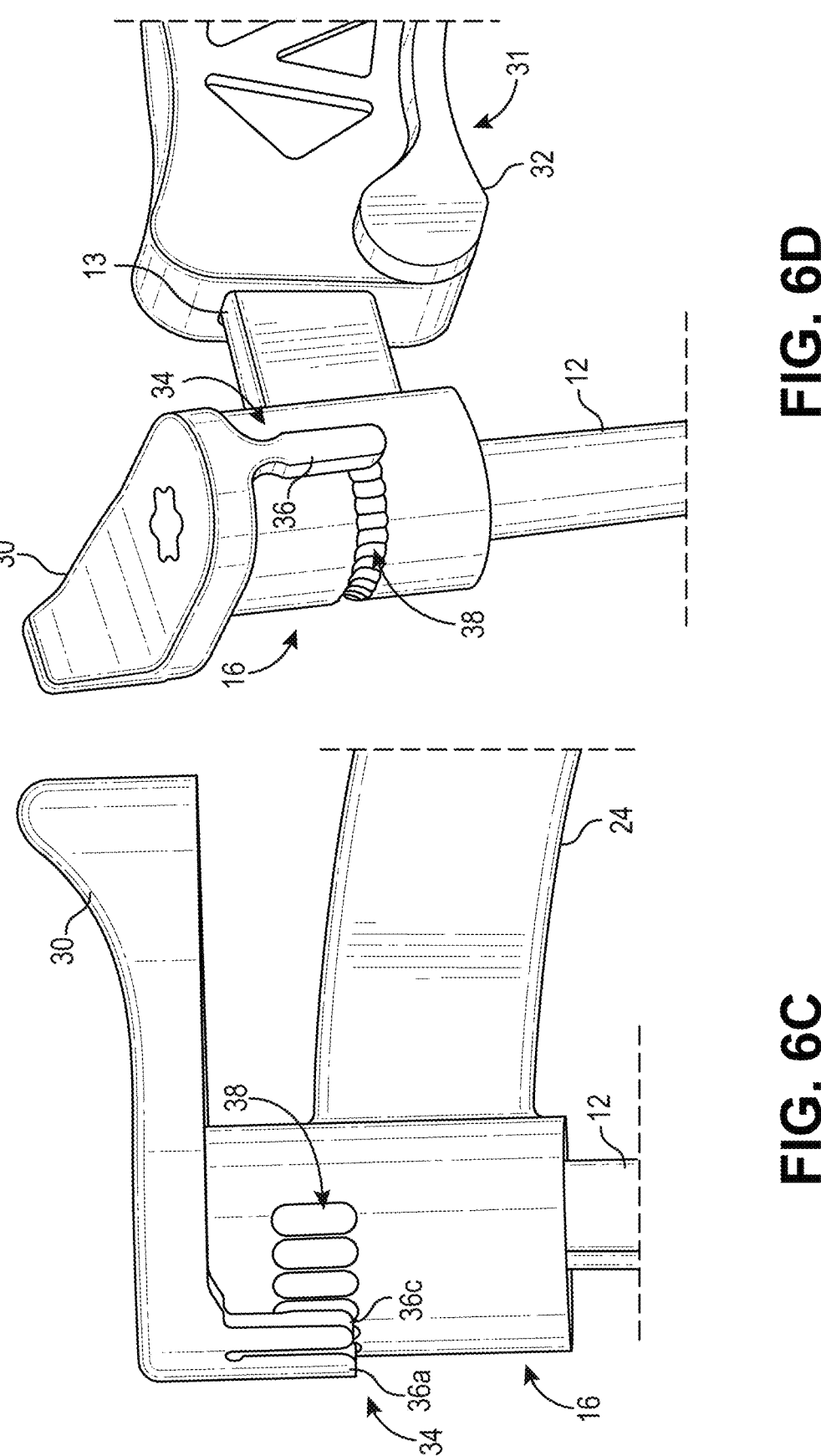
FIG. 6C is a detailed side view of a lever for rotating a guide arm of an apparatus for positioning a drill for forming a bone passage during surgery, according to some embodiments of the present disclosure.
FIG. 6D is a detailed front perspective view of a lever for rotating a guide arm of an apparatus for positioning a drill for forming a bone passage during surgery with the lever in a first angular position, according to some embodiments of the present disclosure.
Figure 6E:
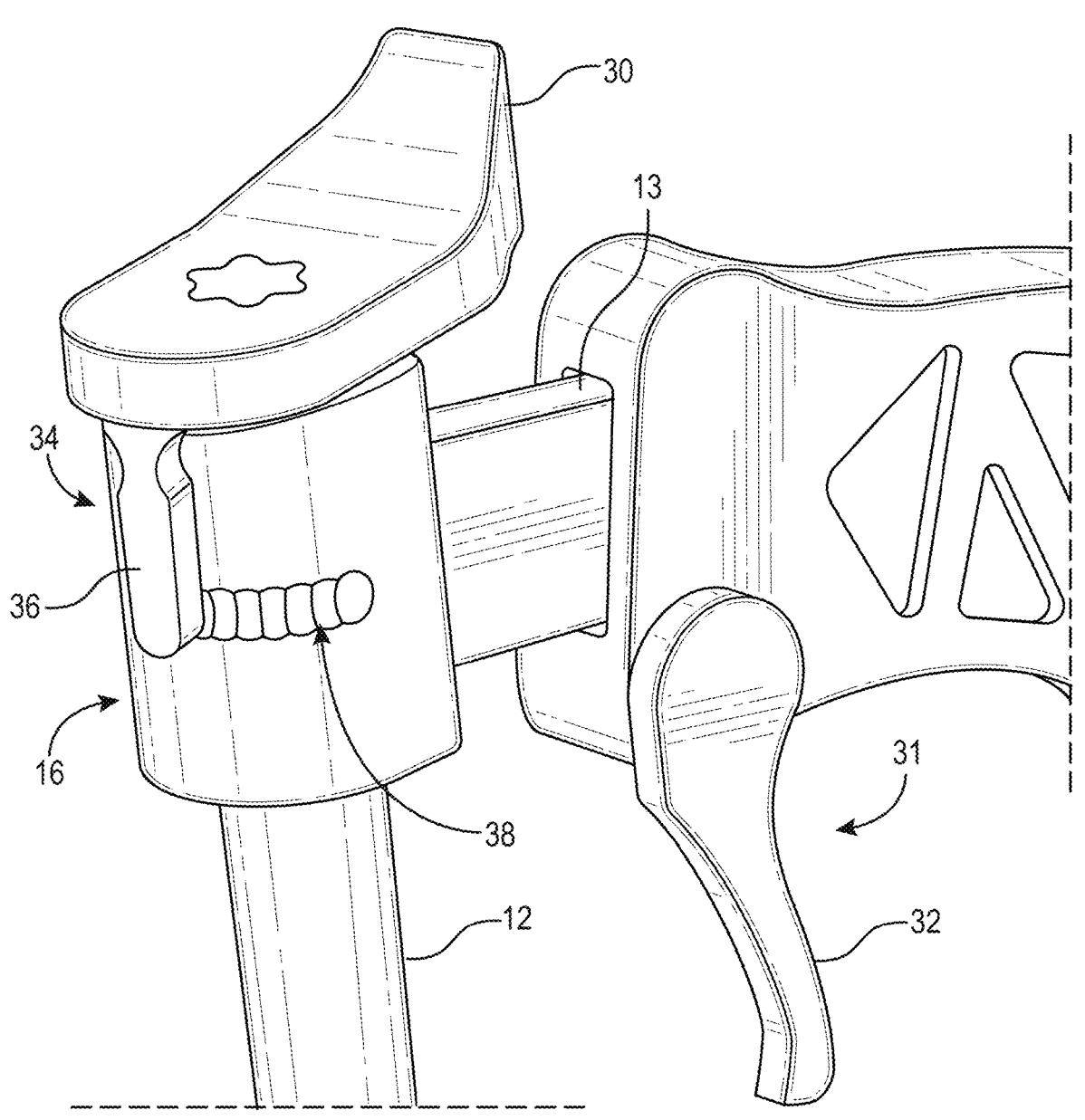
FIG. 6E is a detailed perspective view of a lever for rotating a guide arm of an apparatus for positioning a drill for forming a bone passage during surgery with the lever in a second angular position, according to further embodiments of the present disclosure.
Figure 6G:
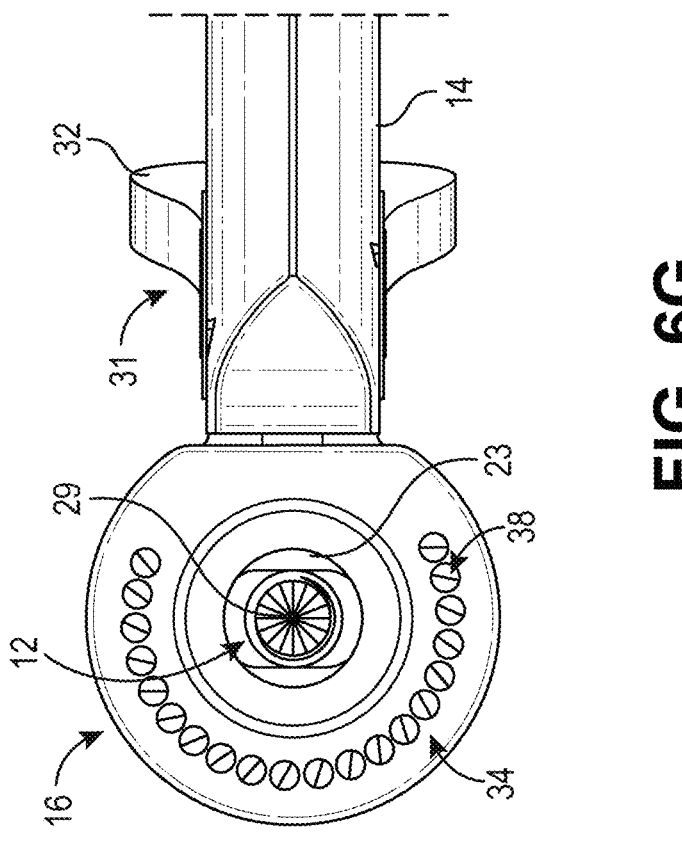
FIG. 6G is a detailed upper view of a cuff with ribs for positioning a drill for forming a bone passage during surgery, according to further embodiments of the present disclosure.
Figure 6F:
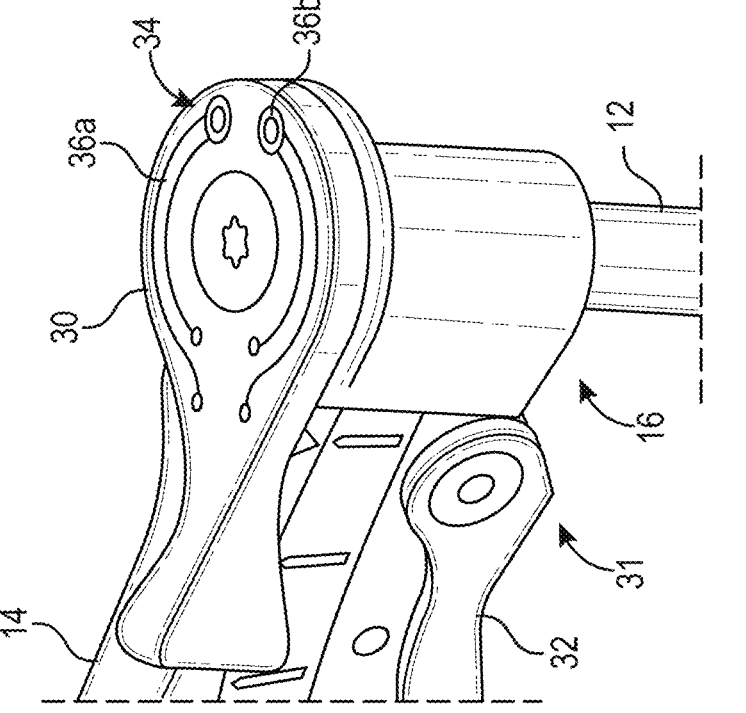
FIG. 6F is a detailed upper perspective view of a lever for rotating a guide arm of an apparatus for positioning a drill for forming a bone passage during surgery, according to further embodiments of the present disclosure.

As shown with additional reference to FIG. 6G, the cuff passage 23 may be defined through the cuff 16. The key 27 may be advanced into the cuff passage 23 (and thus within the cuff 16) and the fastener 37 may be inserted through the lever 30 and into the cuff passage 23, such that the fastener 37 may be guided through the threading 29 on the key 27. Accordingly, the fastener 37 and the key 27 of the guide arm 12 may be engaged within the cuff passage 23 of the cuff 16. In turn, the cuff 16, and thus the neck 24, may be "sandwiched" between the fastener 37 and the guide arm 12.

As discussed in greater detail below, the guide arm 12 may be angularly movable relative to the cuff 16 while being angularly fixed relative to the lever 30, such that the lever 30 may be used to rotate the guide arm 12 relative to the cuff 16 (and thus the neck 24). In other words, the guide arm 12 may be conjured to be angularly movable in rotation relative to the cuff 16 in response to the rotation of the lever 30.

Figure 5B:
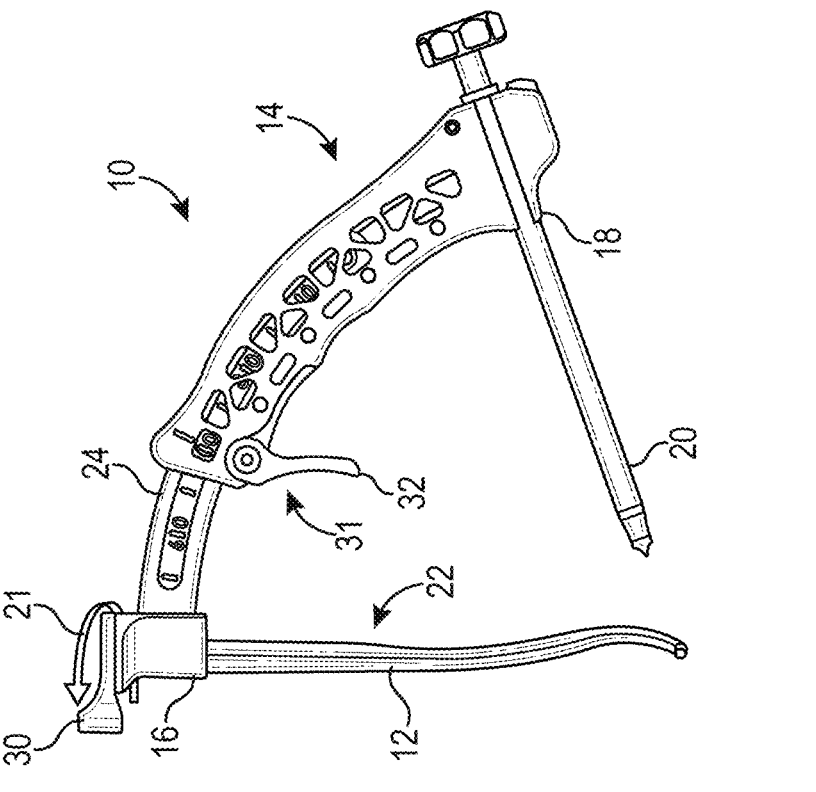
FIG. 5B is a side view of the apparatus of an apparatus for positioning a drill for forming a bone passage during surgery with a guide arm being rotated relative to a sleeve of the apparatus, according to further embodiments of the present disclosure.
Figure 5A:
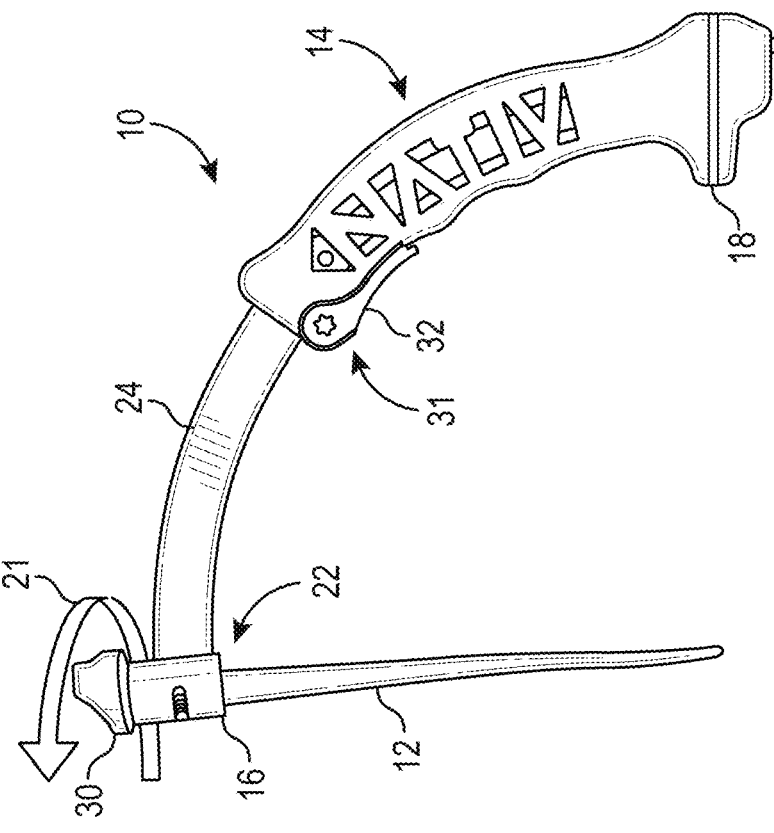
FIG. 5A is a side view of the apparatus of an apparatus for positioning a drill for forming a bone passage during surgery with a guide arm being rotated relative to a sleeve of the apparatus, according to some embodiments of the present disclosure.
Figure 6I:
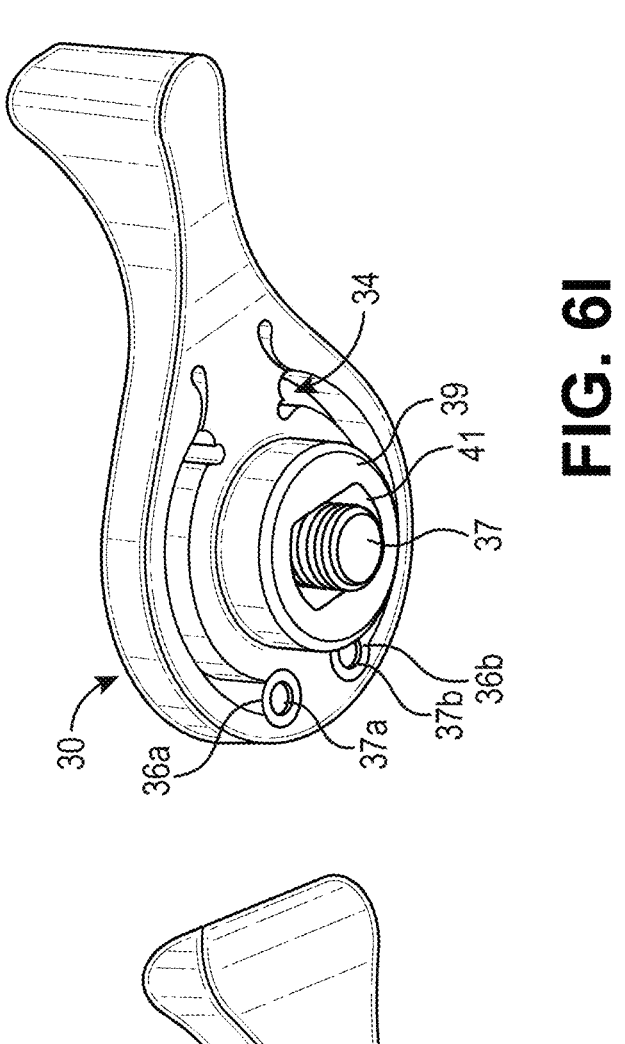
FIG. 6I is a lower perspective view of a lever for rotating a guide arm of an apparatus for positioning a drill for forming a bone passage during surgery, according to further embodiments of the present disclosure.
Figure 6H:
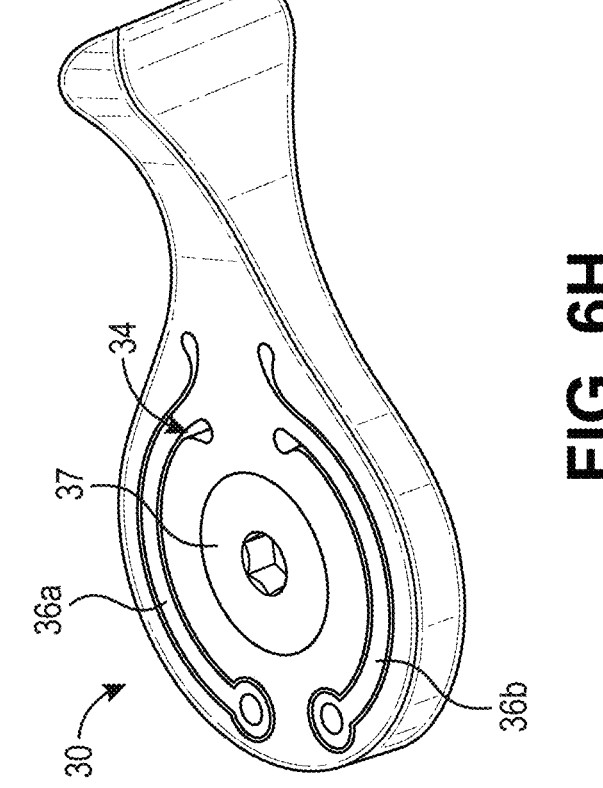
FIG. 6H is an upper perspective view of a lever for rotating a guide arm of an apparatus for positioning a drill for forming a bone passage during surgery, according to further embodiments of the present disclosure.

Referring now to FIGS. 5A and 5B, the apparatus 10 is shown with the guide arm 12 being angularly rotated relative to the cuff 16, according to some embodiments of the present disclosure. The lever 30 may be configured to be rotated such that the guide arm 12 is rotated within the cuff passage 23 of the cuff 16 (e.g., about the second longitudinal axis 54 of the guide arm 12). For example, and as shown with additional reference to FIG. 6I, the lever 30 may include a round insert 39 which may be advanced into the cuff passage 23 (shown with additional reference to FIG. 6G) of the cuff 16. In turn, and as shown with additional reference to FIG. 6I, the round insert 39 may include a keyed recess 41. The key 27 of the guide arm may be configured to be advanced into the keyed recess 41 of the lever 30, such that angular movement of the lever 30 is transferred to angular movement of the guide arm 12. Accordingly, in some embodiments, the cuff 16 may be configured to allow the guide arm 12 to rotate approximately forty-five degrees in either direction via the lever 30. The arrangement of the fastener 37, the round insert 39, and the key 27 is further depicted with additional reference to FIG. 7D.

In some embodiments, the lever 30 and the guide arm 12 are formed as a single component. In other embodiments, and as mentioned above with reference to FIG. 4E, the lever 30 is attached to the guide arm 12 via an adhesive or a suitable means of mechanical fixation (e.g., the fastener 37).

As mentioned above, and with additional reference to FIG. 10, the handle 14 may be configured to be gripped in the hand 99 of the user. In some embodiments, the lever 30 may be configured to be rotated by a thumb 98 of the hand 99. In other words, the lever 30 may be actuated (e.g., pressed, pushed, etc.) by the user's thumb 98. For example, and as depicted in greater detail with reference to FIGS. 6A-6I, the lever 30 may be contoured such that the user's thumb may rotate the lever 30 through an angular rotation 21 whilst the user's hand remains gripped about the handle 14. In this sense, the lever 30 may be considered a thumb lever. While the lever 30 is depicted as being actuated after the handle 14 has been extended away from the guide arm 12, it should be appreciated that the lever 30 may be similarly actuated in any position of the handle 14 relative to the guide arm 12, including the positions depicted with reference to FIGS. 2B and 2F. It should be appreciated that the depicted embodiment of the lever 30 is exemplary in nature, and that the lever 30 may be provided in any configuration suitable for facilitating rotation of the guide arm 12. For instance, in other embodiments, the lever 30 may be provided as a knob.

As suggested above, the lever 30 may be actuated to rotate the guide arm 12 attached thereto within the cuff 16 and, thus, rotate the guide arm 12 through the angular rotation 21. Accordingly, the handle 14 may be rotated and translated (depending on the distance by which the handle 14 has been extended away from the guide arm 12 as discussed above with reference to FIGS. 3A-3D) relative to the guide arm 12 based on actuation of the lever 30. For instance, and as discussed in greater detail below with reference to FIGS. 11A-11B, when the tip 26 is placed in contact with the meniscal root insertion of the tibial plateau 114, the handle 14 may need to be rotated relative to the knee 110 in order to properly position the sleeve 20 relative to the knee 110. In order to facilitate such rotation without disengaging the tip 26 from the tibial plateau 114, the lever 30 may be actuated in order to facilitate a controlled rotation of the handle 14 relative to the guide arm 12.

As discussed in greater detail below, the apparatus 10 may further include a detent mechanism 34 configured to provide resistance against the rotation of the lever 30. In this sense, the detent mechanism 34 may be configured to provide resistance against the rotation of the guide arm 12 relative to the cuff 16.

Referring now to FIGS. 6A-6I, the cuff 16 and lever 30 are shown in greater detail, according to various embodiments of the present disclosure. In some embodiments, the cuff 16 includes the detent mechanism 34. The detent mechanism 34 may be configured to provide a resistance (e.g., frictional, biased, lock-in-place, etc.) against the rotation of the guide arm 12 relative to the cuff 16. In particular, the detent mechanism 34 may be configured to maintain the angular position of the guide arm 12 relative to the cuff 16 (and thus the handle 14) when the guide arm 12 is not being rotated by actuation via the lever 30 as described above. Accordingly, the detent mechanism 34 may be configured to prevent inadvertent rotational movements of the guide arm 12 relative to the handle 14.

The detent mechanism 34 may include a number (e.g., series) of ribs 38 (e.g., divots) and one or more detent arms 36 configured to mechanically engage one or more of the number of ribs 38. The ribs 38 may be defined on the cuff 16. For example, the ribs 38 may be distributed along the outer curved surface of the cuff 16. In other words, the ribs 38 may be recessed in an elongated channel below the surface of the cuff 16. Each of the detent arm(s) 36 may include a projection (e.g., a tooth) configured to fit within a segment of the ribs 38. In order to provide the aforementioned resistance against the rotation of the guide arm 12 relative to the cuff 16, the detent arm(s) 36 may be defined on the lever 30. In this sense, the detent arm(s) 36 may be considered a component of the lever 30. In other embodiments, the detent arm(s) 36 may be disposed on and extend from the lever 30.

Once the projection(s) of the detent arm(s) 36 are positioned within a segment of the ribs 38, the detent arm(s) 36 may provide a biasing force that maintains the position of the projection(s) within the segment of the ribs 38, thereby retaining the orientation of the guide arm 12 until a threshold amount of force is applied to the lever 30 (thereby moving the projection(s) of the detent arm(s) 36 to an adjacent segment of the ribs 38). Of course, the ribs 38 (e.g., the segments thereof) may be spaced at particular intervals in order to provide precise orientation of the guide arm 12.

In some embodiments, the arrangement of the ribs 38 provides for a resting angular position of the guide arm 12 relative to the cuff 16 every six degrees. In other embodiments, the arrangement of the ribs 38 provides for such resting angular position every seven degrees. In other embodiments still, the arrangement of the ribs 38 provides for some other suitable distribution of resting angular positions of the guide arm 12 relative to the cuff 16.

In some embodiments, and as shown with particular reference to FIGS. 6A-6E, the detent arm(s) 36 extends downward from the lever 30. In turn, the ribs 38 may be defined on a curved outer profile of the cuff 16, such that the projection(s) of the detent arm(s) 36 extend inward (e.g., radially inward) from the detent arm(s) 36 in order to engage the ribs 38. In other embodiments, and as shown with particular reference to FIGS. 6F-6I, the detent arm(s) 36 are integrated with the flat profile of the lever 30. In other words, the detent arm(s) 36 may be defined by one or more cuts defined in the surface of the lever 30, and in some cases be coplanar with the upper surface of the lever 30. In turn, the ribs 38 may be defined along a curved path on an upper surface of the cuff 16, such that the projection(s) of the detent arm(s) 36 extend downwards from the detent arm(s) 36 in order to engage the ribs 38. Accordingly, in some embodiments the engagement of the detent mechanism 34 is provided on the side of the cuff 16 (as shown with particular reference to FIGS. 6A-6E), while in other embodiments the engagement of the detent mechanism 34 is provided on the top of the cuff 16 (as shown with particular reference to FIGS. 6F-6I).

In some embodiments, and as shown with particular reference to FIGS. 6A, 6D, and 6E, the detent arm(s) 36 are configured as a single member (e.g., the detent arm 36). In other embodiments, and as shown with particular reference to FIGS. 6B, 60, 6F, and 6H, the detent arm(s) 36 may be configured as a number of members. As a first example, and as shown with particular reference to FIGS. 6F and 6H, the detent arm 36(*s*) may be configured as two members: a first detent arm 36*a* and a second detent arm 36*b*. As a second example, and as shown with particular reference to FIGS. 6B and 6C, the detent arm 36(*s*) may be configured as three members: the first detent arm 36*a*, the second detent arm 36*b*, and the third detent arm 36*c*. In further embodiments, the detent arm(s) 36 are configured as four or more members. Depending on the implementation, more than one projection may be provided by a single detent arm 36. For instance, and as shown with particular reference to FIGS. 6B-6C, the first detent arm 36*a* may be wide enough to facilitate a number of projections configured to interact with the ribs 38.

In some embodiments, particularly where the detent arm(s) 36 are configured to facilitate a number of projections as mentioned above, only a portion of the projections (e.g., one of the projections, the projections on only one of the members, etc.) may engage the ribs 38 at a particular time (e.g., at a particular orientation of the guide arm 12), while the other projections rest at the top of the ribs 38. Advantageously, such a configuration may allow for deeper segments of the ribs 38 (and more pronounced corresponding projections), thereby providing enhanced retention of the orientation of the guide arm 12 in a single desired position.

In some embodiments, the detent arm(s) 36 and the cuff 16 are formed as a single component. In other embodiments, the detent arm(s) 36 are attached to the sleeve via an adhesive or some suitable means of mechanical fixation. Accordingly, the detent arm(s) 36 and the ribs 38 may facilitate the ability of the detent mechanism 34 to lock and secure the angular position of the guide arm 12 relative to the cuff 16. However, the detent arm(s) 36 may be configured with suitable flexibility such that the projection(s) are easily pushed from one segment of the ribs 38 to another segment of the ribs 38, thus allowing the user to rotate the guide arm 12 via the lever 30.

In further embodiments, the detent mechanism 34 may be provided in a reverse-orientation than that described above (e.g., a male projection extending from the detent arm(s) 36 to be received within a female segment of the ribs 38). For instance, the detent arm(s) 36 may rather provide a female feature which receives a male feature extending from the ribs 38.

In further embodiments, the detent mechanism 34 may include an additional lock feature configured to be secured over the detent arm(s) 36, thereby preventing (or partially resisting) the ability of the detent arm(s) 36 to act as a spring as described above. In this sense, the projection extending from the detent arm(s) 36 may be prevented from being bending outwards to remove the projection from the present segment of the ribs 38, thus further securing the present orientation of the guide arm 12.

Although the detent mechanism 34 is depicted herein as including the ribs 38 and the detent arm(s) 36 with one or more teeth defined thereon, the detent mechanism 34 may include any suitable components necessary to facilitate securing the angular position of the guide arm 12 as discussed herein. Accordingly, the detent mechanism 34 may include a ball-and-socket configuration, a friction fit configuration, a biased ball bearing on a spring configuration, and so on. The detent mechanism 34 may thus be attached or otherwise integrated with the other components of the apparatus 10 in any form suitable for providing the aforementioned function of securing the angular position of the guide arm 12 relative to the cuff 16.

As discussed in greater detail below, the apparatus 10 may further include a neck locking mechanism 31 disposed on the handle 14. In some embodiments, the neck locking mechanism 31 is configured to hold the neck 24 in place relative to the handle 14 and release the neck 24. For example, the neck locking mechanism 31 may include a hinge 32. The hinge 32 may be angularly movable in rotation relative to the handle 14. For example, the hinge 32 may be movable between a first hinge position where the neck locking mechanism 31 holds the neck 24 in place relative to the first handle passage 15, and a second hinge position where the neck locking mechanism releases the neck 24. In some cases, the hinge 32 may be rotated by an index finger of the user.

Referring now to FIG. 7A-7F, neck locking mechanism 31 is shown in greater detail, according to various embodiments of the present disclosure. As suggested above, the neck locking mechanism 31 may be configured to selectively secure the position of the neck 24 relative to the handle 14. For instance, the lock mechanism may be disposed on the handle 14. The neck locking mechanism 31 may include the hinge 32 movable (along a path 33) between a first hinge position (shown with reference to FIGS. 7A-7D) wherein the neck locking mechanism 31 holds the neck 24 in place relative to the first handle passage 15, and a second hinge position (shown with reference to FIGS. 2A-2D) where the lock mechanism releases the neck 24 (e.g., such that the neck 24 is axially movable in translation relative to the first handle passage 15). In other embodiments, the first hinge position shown with reference to FIGS. 2A-2D is the position of the hinge 32 in which the neck locking mechanism 31 holds the neck 24 in place, while the second position shown with reference to FIGS. 7A-7D is the position of the hinge 32 in which the neck locking mechanism 31 releases the neck 24. Of course, it should be appreciated that the depicted positions of the hinge 32 are exemplary in nature and the aforementioned first and second positions may be afforded through various degrees of rotating the hinge 32.

As suggested above, when the hinge 32 is rotated relative to the handle 14 (e.g., along the path 33) to move from the hinge 32 between the first and/or second hinge positions, the hinge 32 may lock the axial position of the neck 24 relative to the first handle passage 15. After the tip 26 has been engaged with the tibial plateau 114 of the knee 110, and before or after the guide arm 12 has been rotated relative to the handle 14 as discussed above, the neck 24 may be axially translated relative to the first handle passage 15 (as discussed above) in order to suitably position the second handle passage 18 for guiding the sleeve 20 towards the tibia 112 of the knee. Advantageously, once this has been accomplished, the neck locking mechanism 31 may be used to secure this configuration of the apparatus 10 in place in order to allow the user to proceed with advancing the sleeve 20 through the second handle passage 18 in order to form a bone passage within the tibia 112.

Figures 7A, 7B:
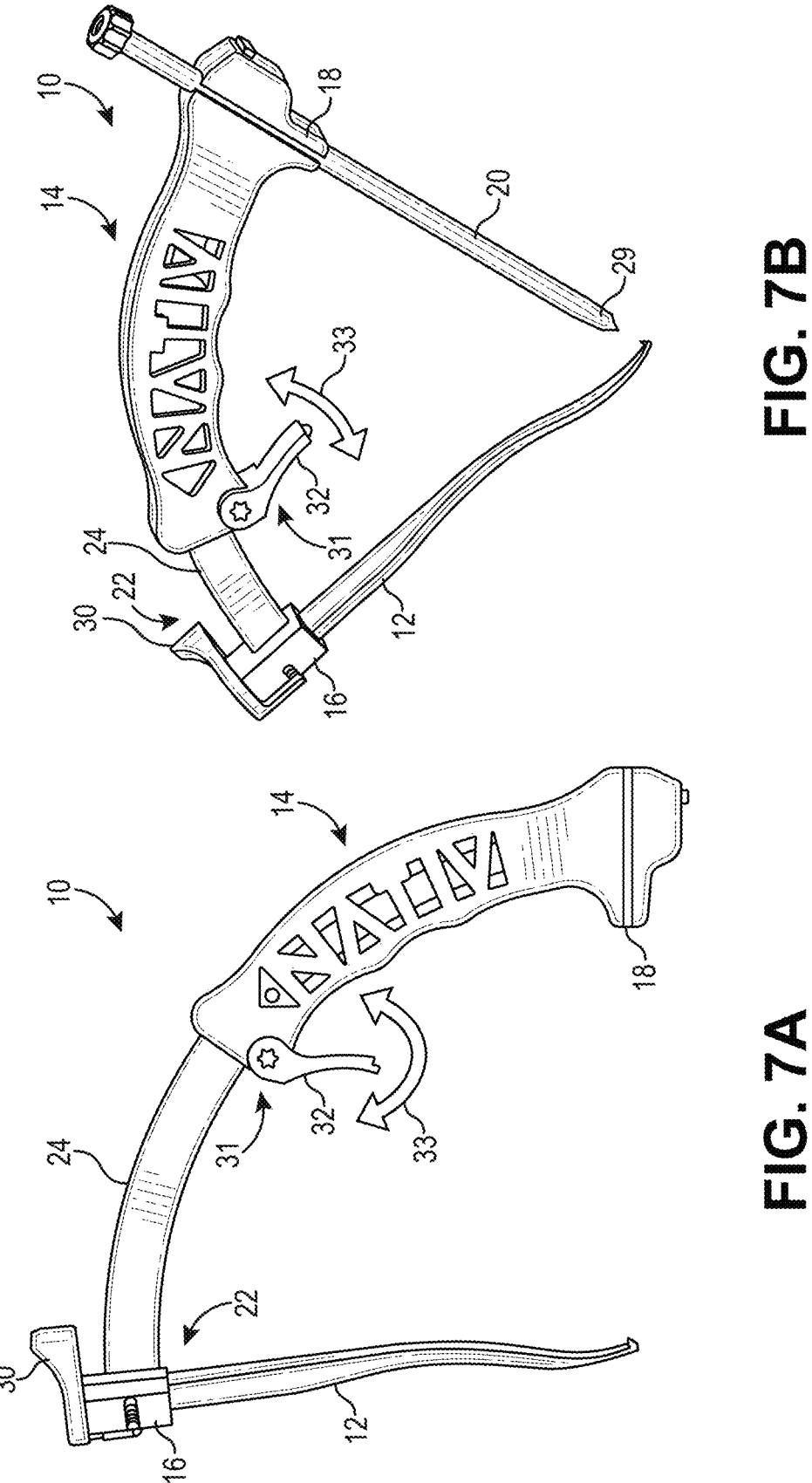
FIG. 7A is a side view of an apparatus for positioning a drill for forming a bone passage during surgery with a hinge of a locking mechanism of the apparatus being rotated to allow the guide arm to move relative to a handle of the apparatus, according to some embodiments of the present disclosure.
FIG. 7B is a side perspective view of an apparatus for positioning a drill for forming a bone passage during surgery with a hinge of a locking mechanism of the apparatus being rotated to allow the guide arm to move relative to a handle of the apparatus, according to some embodiments of the present disclosure.
Figure 7D:
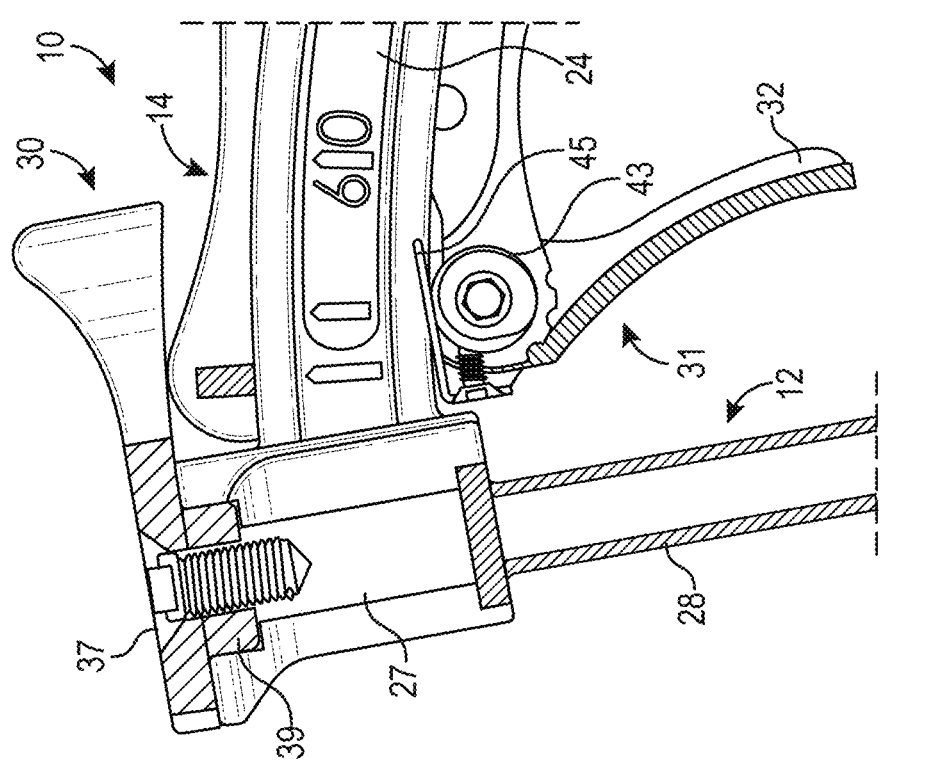
FIG. 7D is a detailed side view of an apparatus for positioning a drill for forming a bone passage during surgery with a hinge of a locking mechanism of the apparatus being rotated to allow the guide arm to move relative to a handle of the apparatus, according to further embodiments of the present disclosure.
Figure 7C:
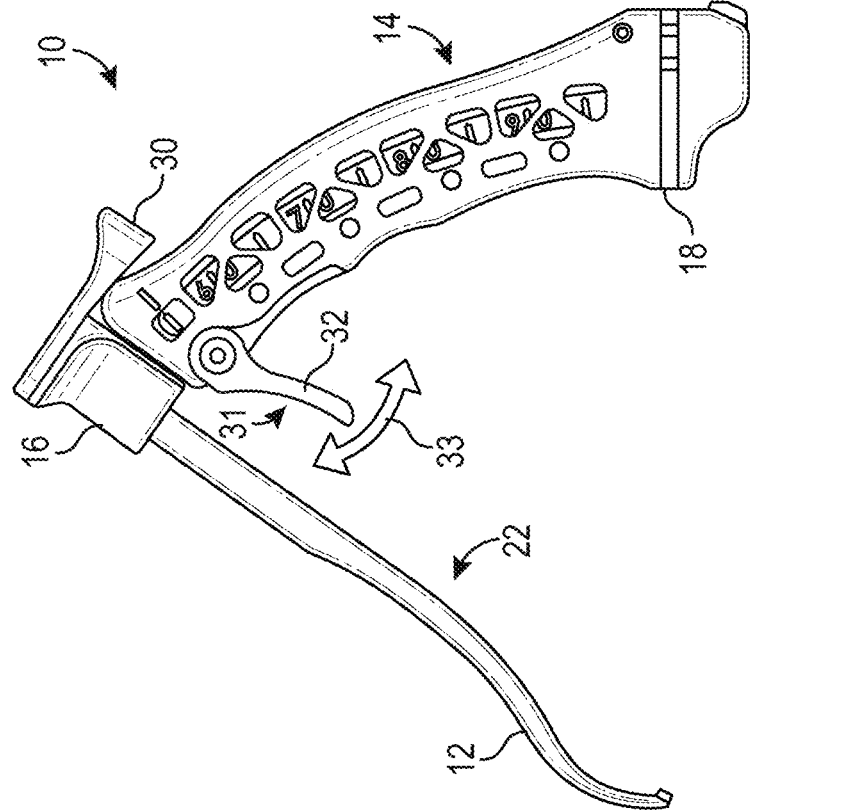
FIG. 7C is a side view of an apparatus for positioning a drill for forming a bone passage during surgery with a hinge of a locking mechanism of the apparatus being rotated to allow the guide arm to move relative to a handle of the apparatus, according to further embodiments of the present disclosure.
Figures 7E, 7F:
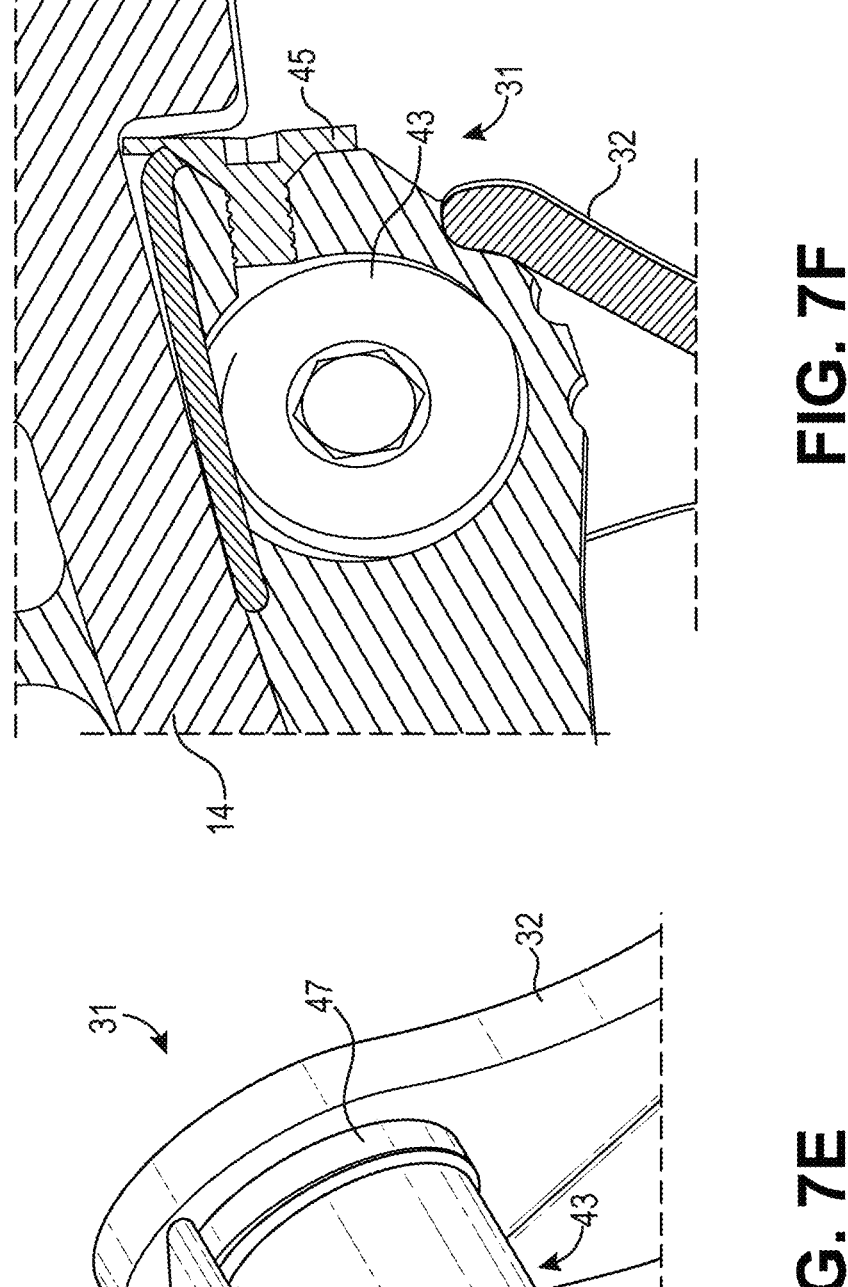
FIG. 7E is an upper perspective view for a cam of an apparatus for positioning a drill for forming a bone passage during surgery, according to further embodiments of the present disclosure.
FIG. 7F is a side perspective view of a cam for an apparatus for positioning a drill for forming a bone passage during surgery, according to further embodiments of the present disclosure.

In some embodiments, and as shown with particular reference to FIGS. 7D-7F, the neck locking mechanism 31 further includes a cam 43 and a shim 45. The cam 43 may be angularly movable in rotation relative to the handle 14 in response to the rotation of the hinge 32. In turn, the shim 45 may be angularly movable in rotation relative to the handle 14 in response to rotation of the cam 43. Accordingly, the cam 43 may be integrated with the hinge 32 such that, when the hinge 32 is rotated as shown, the cam 43 contacts (or, as discussed in greater detail below, facilitates contact with) the neck 24, thus holding the neck 24 in place relative to the handle 14. Thus, the shim 45 may be pivoted by the cam 43 in order to make contact with the neck 24, thereby engaging the neck 24 and holding the neck 24 in place relative to the handle 14 (or, more particularly, the first handle passage 15).

As shown with particular reference to FIGS. 7E and 7F, the cam 43 may include an elliptical track 47 on which the shim 45 is disposed. Thus, when the cam 43 is rotated with the angular movement of the hinge 32, the elliptical track 47 may gradually direct the shim 45 towards the neck 24, until the shim 45 makes contact with the neck 24 and secures the neck 24 in place. Advantageously, the elliptical track 47 may facilitate full articulation of the hinge 32 (suitable for tactile engagement of a user) resulting in the minor pivot required to bring the shim 45 into contact with the neck 24. Of course, it should be appreciated that the neck locking mechanism 31 may include any combination of components suitable for allowing the user to lock the position of the neck 24 relative to the first handle passage 15 as discussed herein.

In some embodiments, the shim 45 may maintain consistent contact with the neck 24 (e.g., over a range of orientations of the hinge 32, or over the entirety of the potential angular orientations of the hinge 32). In this sense, the shim 45 may provide a friction that prevents the neck 24 from moving freely within the handle 14. In some embodiments, the shim 45 is at least partially elastic in order to provide such friction.

Figure 7G:
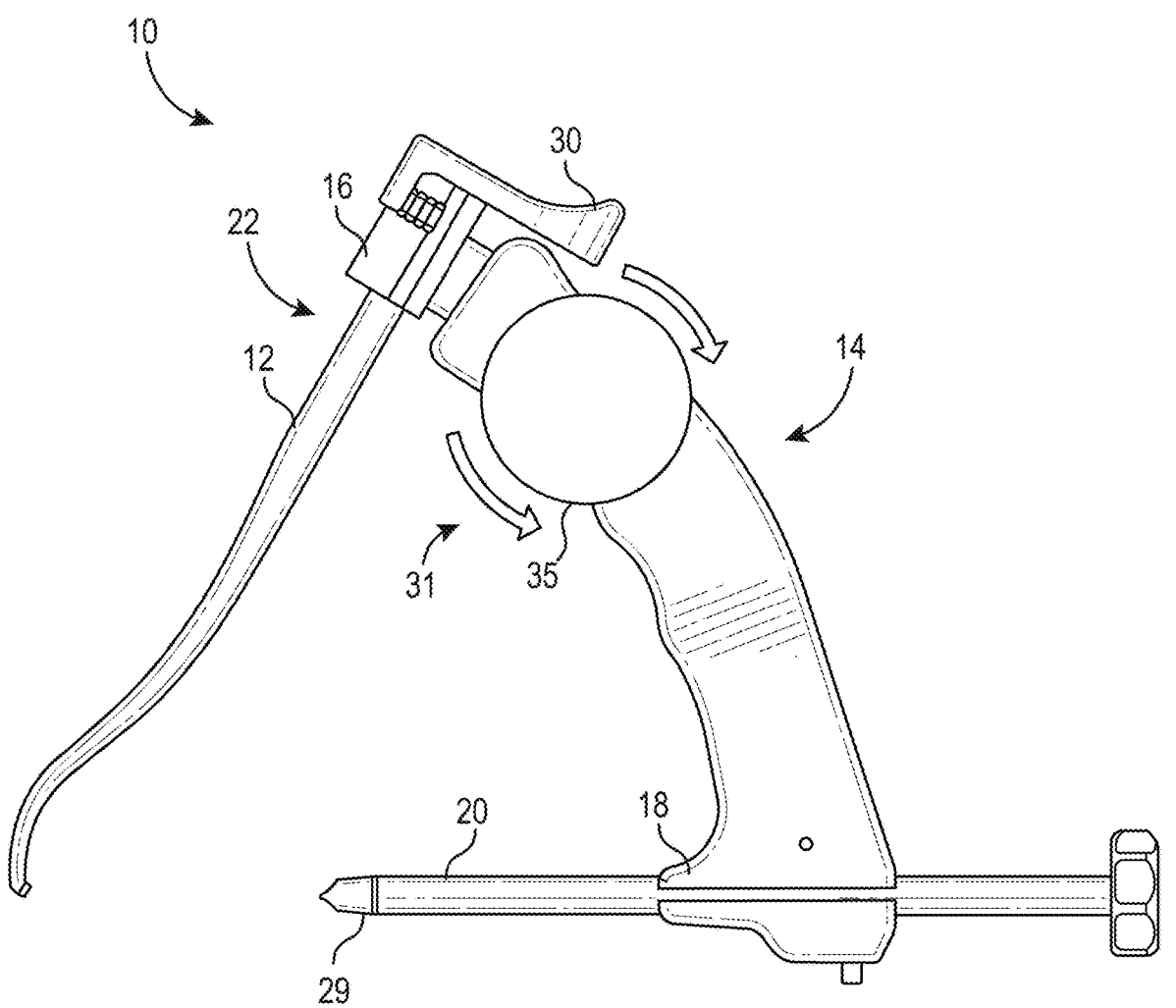
FIG. 7G is a side view of an apparatus for positioning a drill for forming a bone passage during surgery with a screw lock of a locking mechanism of the apparatus being rotated to allow the guide arm to move relative to the handle of the apparatus, according to some embodiments of the present disclosure.

In further embodiments, and with particular reference to FIG. 7G, the neck locking mechanism 31 may include a screw lock 35. For instance, the screw lock 35 may be rotated in either direction in order to rotate a screw member relative to threading on the handle 14, thus moving the screw member towards or away from the neck 24 therein. When the screw lock 35 is rotated such that the screw member engages the neck 24, the screw lock 35 may thus secure the neck 24 in place relative to the handle 14.

Referring again to FIGS. 2B-2D and 2F-2H, the apparatus 10 may include the sleeve 20, according to various embodiments of the present disclosure. As suggested above, the sleeve 20 may be received within the second handle passage 18 of the handle 14, and the drill 29 may be axially movable within the sleeve 20. Depending on the implementation, the sleeve 20 may facilitate, in addition to a drill mechanism suitable for forming a bone passage during surgery, a punch guide, a punch, or other suitable member for inserting such a drill mechanism into a bone passage. The second handle passage 18 may be formed on a second end of the handle 14 opposite the first end that forms the handle opening 13. Depending on the implementation, the sleeve 20 may be inserted within the second handle passage 18, and the drill 29 may be inserted within the sleeve 20, before or after any of the various steps discussed herein, in order to position and guide the sleeve 20 for forming bone passages during a surgical procedure.

Figures 8A, 8B:
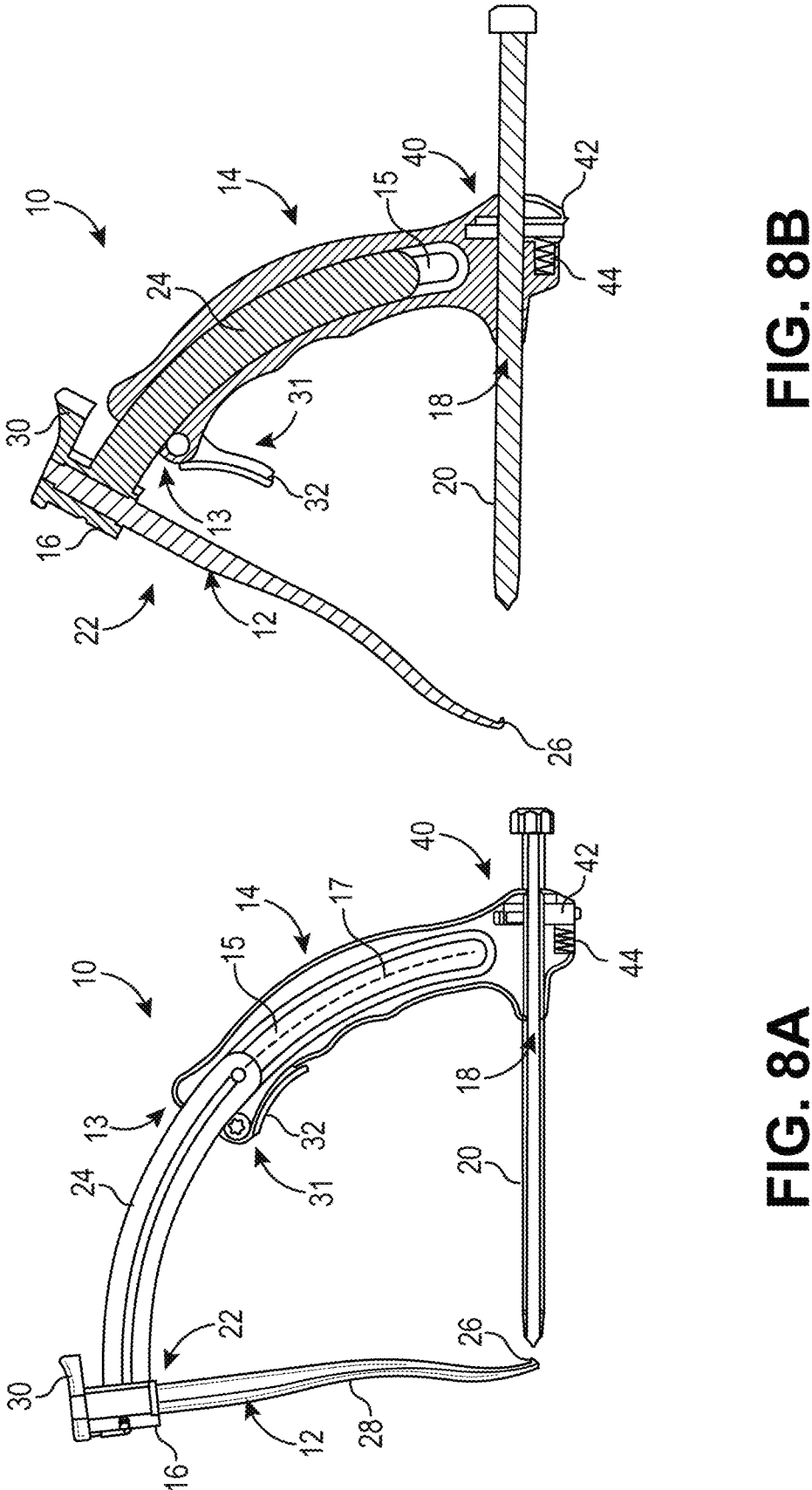
FIG. 8A is a detailed side cross-sectional view of an apparatus for positioning a drill for forming a bone passage during surgery, according to some embodiments of the present disclosure.
FIG. 8B is a side cross-sectional view of an apparatus for positioning a drill for forming a bone passage during surgery, according to some embodiments of the present disclosure.
Figure 8C:
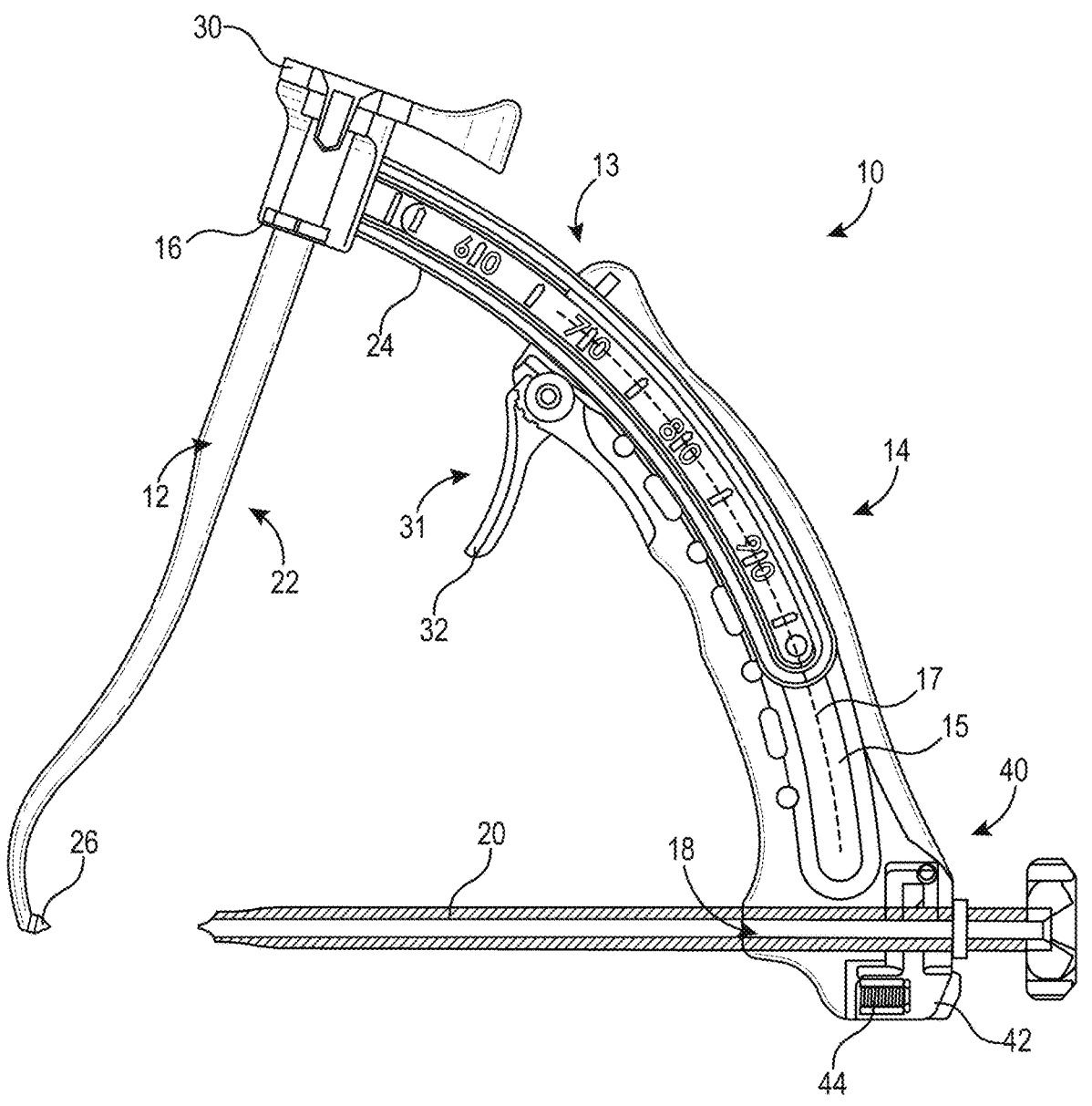
FIG. 8C is a detailed side cross-sectional view of an apparatus for positioning a drill for forming a bone passage during surgery, according to further embodiments of the present disclosure.

Referring now to FIGS. 8A-8C, cross-sectional views of the apparatus 10 is shown, according to various embodiments of the present disclosure. As mentioned above with reference to FIG. 3A-3D, the guide arm assembly 22 may include the neck 24 that is disposed within the first handle passage 15 of the handle 14 and is axially movable in translation relative to the first handle passage 15, thus allowing extension of the apparatus 10 along the path 19. For instance, the neck 24 and the handle 14 may be joined in a sliding relationship along an arc shaped path that follows an arcuate axis 17 of the first handle passage 15. In other words, the neck 24 and the handle 14 (or more, particular, the first handle passage 15) may feature corresponding arcuate shapes. As shown, the first handle passage 15 may begin near the first end of the handle 14 that forms the handle opening 13 and terminate near the second end of the handle 14 that forms the second handle passage 18.

Although the neck 24 and the first handle passage 15 are generally discussed above in a male-female configuration (e.g., the neck 24 is passed into and through the first handle passage 15), in further embodiments, the neck 24 and the first handle passage 15 may be provided in a female-male configuration (e.g., the neck 24 is configured with a recess that is configured to allow the handle 14 to be received therein and passed therethrough. In this sense, the neck 24 may be configured as a handle that is gripped by the hand 99 of the user, allowing the handle that is gripped by the hand 99 to be positioned closer to the guide arm 12.

The arcuate axis 17 may be of constant radius such that the apparatus 10 is adjustable between a first position (as shown with additional reference to FIGS. 2A, 2D, and 2E) in which the first longitudinal axis 52 of the second handle passage 18 and a second longitudinal axis 54 of the guide arm 12 define a first angle 56 between them and a second position (as shown with additional reference to FIGS. 3A and 3C) in which the first longitudinal axis 52 and the second longitudinal axis 54 define a second angle 58 between them that is larger than the first angle 56. Of course, it should be appreciated that the aforementioned first and second positions depicted are exemplary in nature, and the apparatus 10 may be manipulated to reach any number of configurations, in terms of the movement of the neck 24 relative to the first handle passage 15, in order to provide the applications contemplated herein.

As suggested above, the neck 24 and the first handle passage 15 may each have a corresponding arcuate shape (e.g., a curvature that defines part of the perimeter of a circle). In this sense, the neck 24 may be inserted within the first handle passage 15 of the handle 14 (e.g., through the handle opening 13) and axially translated along an axis 17 of the first handle passage 15. In other embodiments, the neck 24 may be coupled to the handle 14 for similar axial translation by some other suitable means (e.g., the neck 24 may be slidably coupled to a track on a side of the handle 14, which maintains the aforementioned arcuate shape). The arcuate shape of the neck 24 and the first handle passage 15 may assure that the tip 26 of the guide arm 12 and the sleeve 20 have a common point of intersection regardless of the position of the neck 24 along the axis 17 of the first handle passage 15.

As discussed in greater detail below, the apparatus 10 may further include a sleeve locking mechanism 40 that is configured to allow the user to advance the sleeve 20 towards the guide arm 12 while also preventing the sleeve 20 from retreating away from the guide arm 12 following such advancement and while the drill within the sleeve 20 is forming a bone passage (e.g., drilling a hole in the tibia 112). The sleeve locking mechanism 40 may include a locking member 42 having a through-hole 46 configured to receive the sleeve 20. The locking member 42 may be movable between an unlocked position where the sleeve 20 is axially movable relative to the through-hole 46 and a locked position where the locking member 42 prevents the sleeve 20 from being moved away from the tip 26. The locking member 42 may be urged by a biasing member 44 towards the locked position.

Figure 9B:
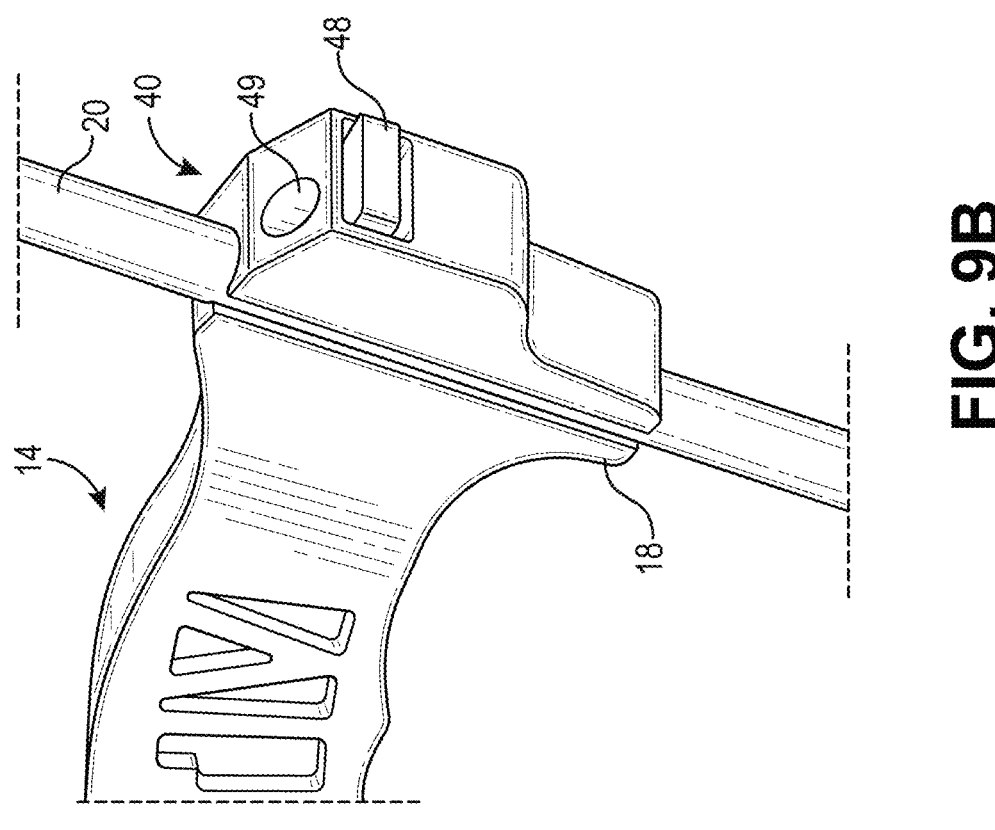
FIG. 9B is a perspective view of an apparatus for positioning a drill for forming a bone passage during surgery showing a drill advancement mechanism of the apparatus in a first position, according to some embodiments of the present disclosure.
Figure 9A:
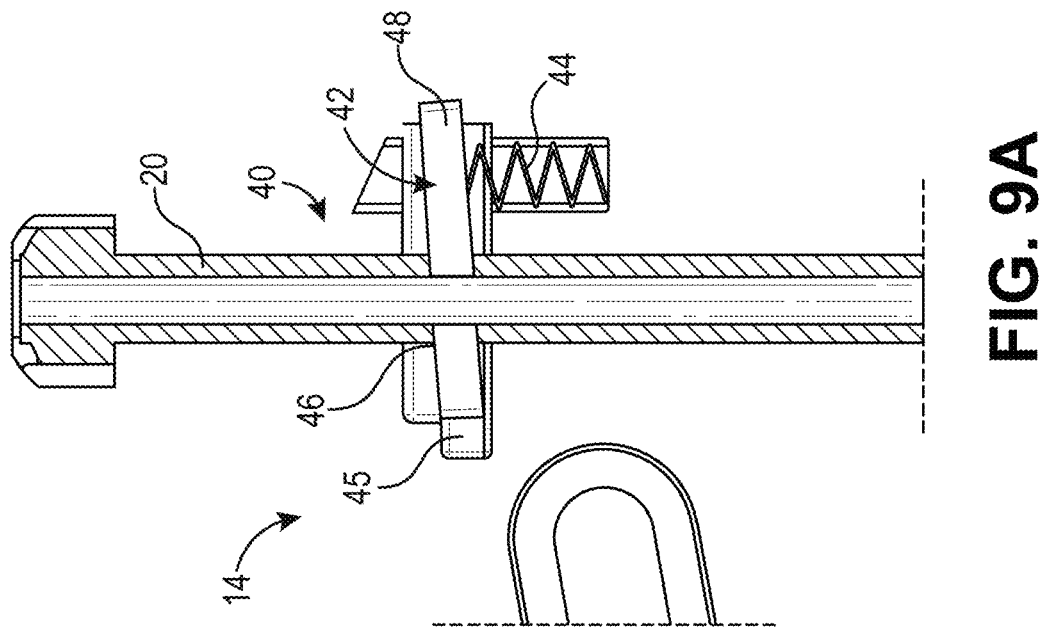
FIG. 9A is a detailed side cross-sectional view of an apparatus for positioning a drill for forming a bone passage during surgery, showing a drill advancement mechanism of the apparatus in a first position, according to some embodiments of the present disclosure.
Figure 9D:
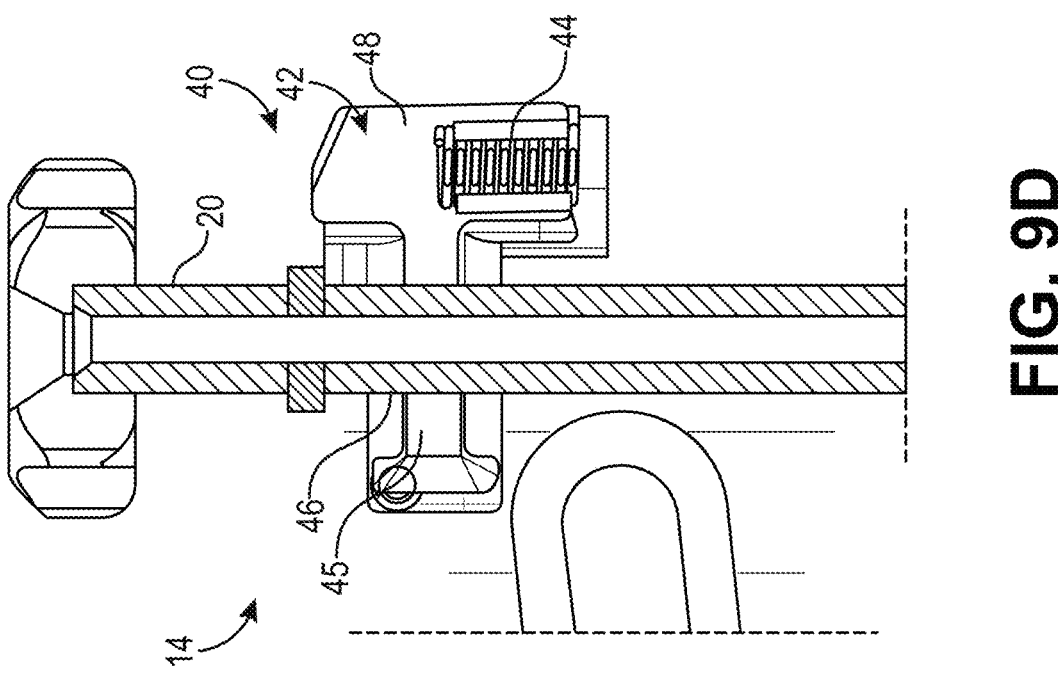
FIG. 9D is a detailed side cross-sectional view of an apparatus for positioning a drill for forming a bone passage during surgery, showing a drill advancement mechanism of the apparatus, according to further embodiments of the present disclosure.
Figure 9C:
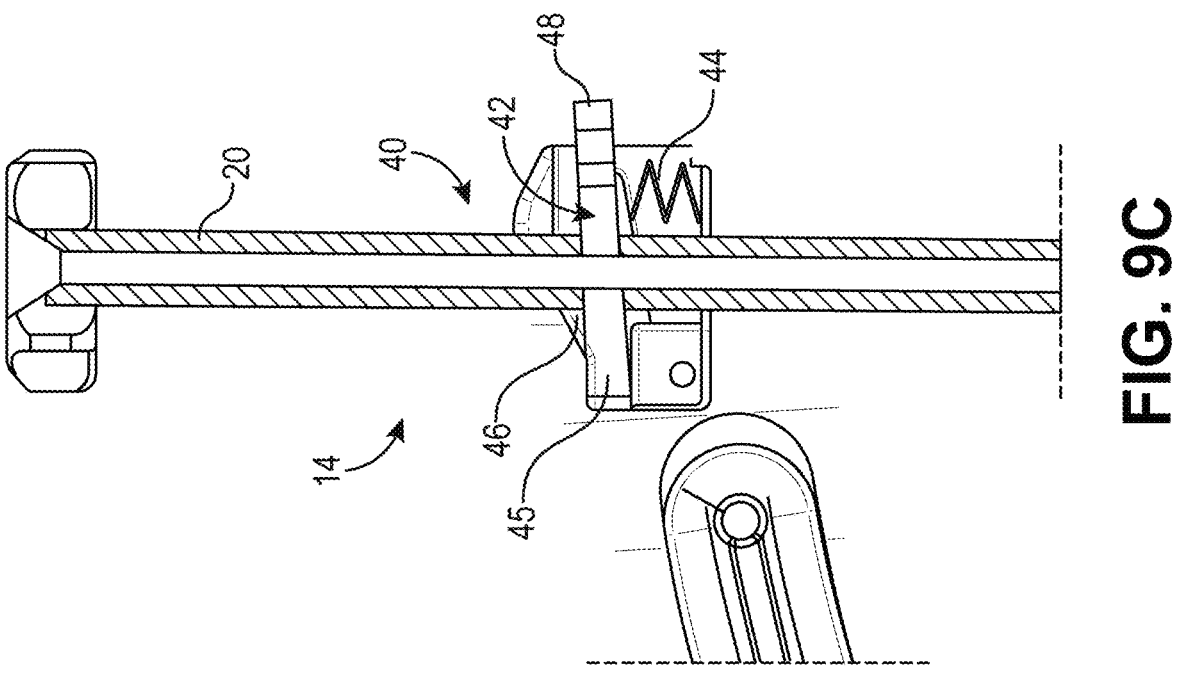
FIG. 9C is a detailed side cross-sectional view of an apparatus for positioning a drill for forming a bone passage during surgery showing a drill advancement mechanism of the apparatus in a second position, according to some embodiments of the present disclosure.

Referring now to FIGS. 9A-9F, the sleeve locking mechanism 40 is shown in greater detail, according to various embodiments of the present disclosure. FIGS. 9A, 9C, and 9D depict side cross-sectional views of the sleeve locking mechanism 40 with the sleeve 20 inserted within the second handle passage 18. The sleeve locking mechanism 40, along with the second handle passage 18, facilitates the positioning and sliding adjustability of the sleeve 20 relative to the handle 14. As discussed in greater detail below, the sleeve locking mechanism 40 may be a one-way lock mechanism including the locking member 42 with the through-hole 46 configured to receive the sleeve 20. The sleeve locking mechanism 40 may be movable between a first unlocked position and a second locked position. The sleeve locking mechanism 40 may further include a biasing member 44 configured to bias the locking member 42 towards the locked position. In the unlocked position, the sleeve 20 may be moved axially in both directions relative to the second handle passage 18 (e.g., towards or away from the tip 26). In the locked position, the sleeve 20 may only be moved axially in one direction, towards the tip 26.

The sleeve locking mechanism 40 may be located on the second end of the handle 14 opposite the first end that forms the handle opening 13. As mentioned above, the sleeve locking mechanism 40 may include the locking member 42 (e.g., a plate, piece, etc.) having the through-hole 46 configured to receive the sleeve 20. For example, the locking member 42 may be made of a relatively thick plate-like material in which a through-hole 46 having a diameter slightly greater than the sleeve 20 is formed. The locking member 42 may be supported by the sleeve 20 by insertion of the sleeve 20 in the through-hole 46 so that the locking member 42 is slidable in the axial direction of the sleeve 20 and movable with respect to the sleeve 20 with some clearance between the through-hole 46 and the outer circumference of the sleeve 20. As discussed in greater detail below, the locking member 42 may be movable between the unlocked position where the sleeve 20 is axially movable relative to the through-hole 46 (and is thus axially movable towards or away from the tip 26 through the second handle passage 18) and the locked position where the locking member 42 secures the sleeve 20 such that the dill sleeve 20 may only be moved axially in one direction, towards the tip 26 in place relative to the through-hole 46.

As mentioned above, the sleeve locking mechanism 40 may further include the biasing member 44 (e.g., a spring). The locking member 42 may be urged by the biasing member 44 towards the aforementioned locked position. For example, the biasing member 44 may be positioned on the handle 14 such that the biasing member 44 pushes the locking member 42 upwards and away from the guide arm 12. In this sense, the biasing member 44 may urge a free end 48 of the locking member 42 upwards, such that the locking member 42 rotates about a pivot end 45 secured to the handle 14.

As mentioned above, the sleeve locking mechanism 40 of the handle 14 may be configured to allow the user to advance the sleeve 20 towards the guide arm 12 while also preventing the sleeve 20 from retreating away from the guide arm 12 following such advancement. For instance, when the sleeve 20 has been properly positioned as discussed above and is then advanced forward (e.g., towards the tibia 112 and the guide arm 12), the locking member 42 may move together with the sleeve 20 while maintaining a frictional engagement with the sleeve 20. When the sleeve 20 is pushed towards the guide arm 12 by the user, the biasing member 44 is compressed by the locking member 42 according to the movement of the sleeve 20, such that an angle of inclination of the locking member 42 with respect to the sleeve 20 is changed and the frictional engagement of the through-hole 46 with the sleeve 20 is weakened. Accordingly, during such forward motion of the sleeve 20, the locking member 42 remains in the position to allow the movement of the sleeve 20 towards the tip 26. When the sleeve 20 is no longer being pushed forward by the user, the angle of inclination of the locking member 42 becomes larger by the action of the biasing member 44, and the locking member 42 is again brought into frictional engagement with the sleeve 20. Thus, the sleeve 20 is prevented from inadvertent movement away from the guide arm 12, such as movement away from the guide arm 12 from a kick-back force caused by drill 29 within the sleeve 20 drilling into bone.

When the user desires to retract the sleeve 20, the user may press the free end 48 of the locking member 42 towards the guide arm 12, thus moving the locking member 42 to the unlocked position, removing the frictional engagement between the locking member 42 and the sleeve 20, and allowing for retraction of the sleeve 20. In this sense, in the unlocked position, the sleeve 20 may also be moved towards the tip 26. In some embodiments, the sleeve locking mechanism 40 further includes an access hole 49 facilitating insertion of a member (e.g., a rod), such that the free end of the locking member 42 is pressed towards the guide arm 12 as mentioned above.

Figure 9F:
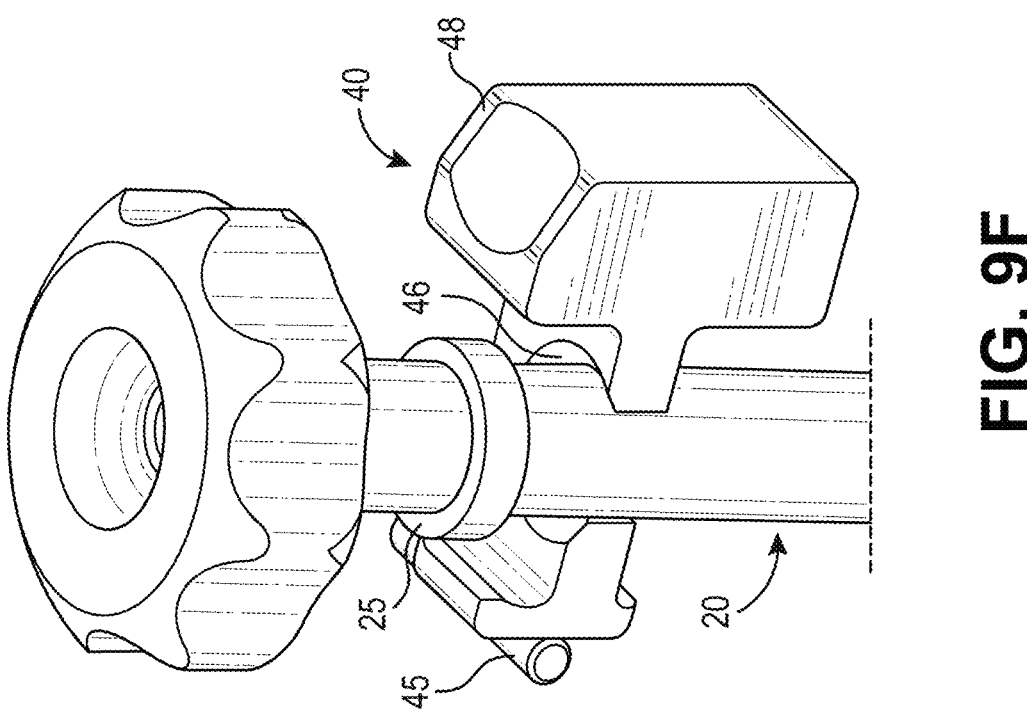
FIG. 9F is a detailed upper perspective view of an apparatus for positioning a drill for forming a bone passage during surgery showing a drill advancement mechanism of the apparatus, according to further embodiments of the present disclosure.
Figure 9E:
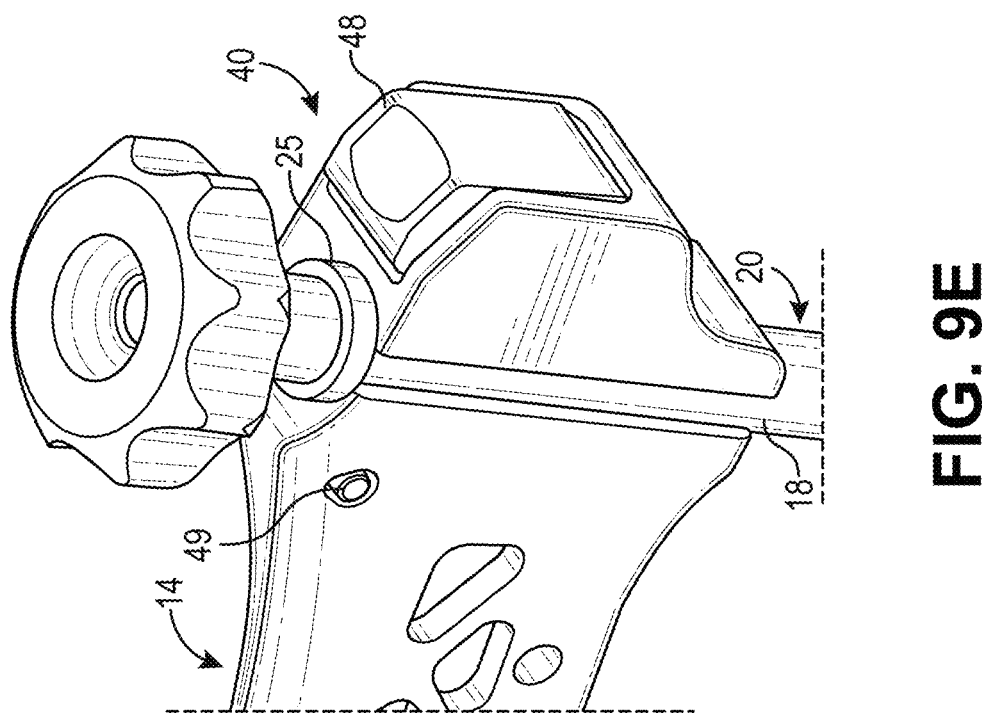
FIG. 9E is an upper perspective view of an apparatus for positioning a drill for forming a bone passage during surgery showing a drill advancement mechanism of the apparatus, according to further embodiments of the present disclosure.

In some embodiments, and as shown with particular reference to FIGS. 9D-9F, the sleeve 20 may include a ring 25. The ring 25 may provide a mechanical stop against the surface of the handle 14 in order to limit the advancement of the sleeve 20 towards the guide arm 12.

As discussed in greater detail below, the present disclosure further provides for a method of positioning and guiding the drill 29 for forming a bone passage during surgery on the knee 110. The method may include providing the handle 14, the neck 24 (including the cuff 16, depending on the implementation), the sleeve 20, and the guide arm 12, as discussed above. The method may further include advancing the guide arm 12 through the anterolateral portal 134 of the knee 110 and positioning the tip 26 of the guide arm 12 on the tibial plateau 114 of the knee 110. The method may further include moving the neck 24 in translation relative to the handle 14, and moving the sleeve 20 in translation relative to the handle 14, such that the sleeve 20 is advanced towards the knee 110. The method may further include angularly moving the lever 30 in rotation relative to the neck 24, such that the guide arm 12 is angularly moved in rotation relative to the neck 24 in response to the rotation of the lever 30. Furthermore, the method may include engaging the neck locking mechanism 31, such that the neck 24 is held in place relative to the handle 14. In some embodiments, the method further includes viewing, via a camera 50, one or more images of the tibial plateau 114 via the anteromedial portal 136 of the knee 110. The method may further include advancing the sleeve 20 through the second handle passage 18 of the handle 14 and towards the knee 110.

Figures 11A, 11B:
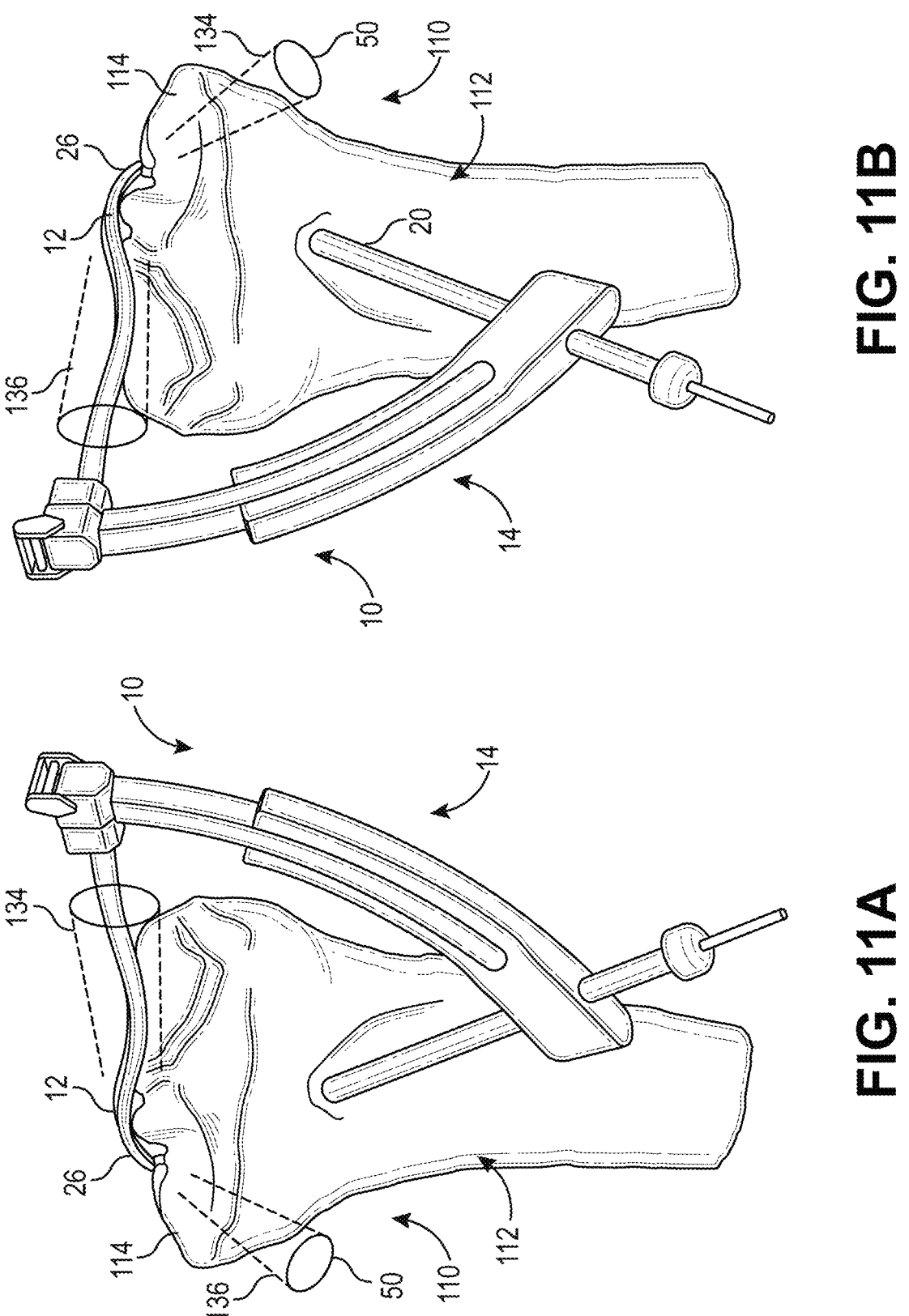
FIG. 11A is a perspective view of an apparatus for positioning a drill for forming a bone passage during surgery, where a guide arm of the apparatus is being engaged with a tibial plateau of the knee via an anterolateral portal of the knee, according to some embodiments of the present disclosure.
FIG. 11B is a perspective view of an apparatus for positioning a drill for forming a bone passage during surgery, where a guide arm of the apparatus is being engaged with a tibial plateau of the knee via an anteromedial portal of the knee, according to some embodiments of the present disclosure.

Referring now to FIGS. 11A-11B, the apparatus 10 is shown engaging the knee 110, according to various embodiments of the present disclosure. In particular, and as shown with reference to FIG. 11A, the guide arm 12 (the tip 26, in particular) is shown engaged with the tibial plateau 114 of the tibia 112 below a femur via the anterolateral portal 138 of the knee 110, thus allowing the tip 26 to grip the tibial plateau 114 while the apparatus 10 is maneuvered as discussed herein to navigate the sleeve 20 into position for forming a bone passage in the knee 110 (via the drill inserted within the sleeve 20) during surgery. For instance, the tip 26 may be navigated through the anterolateral portal 138 of the knee 110, such that the tip 26 grips the tibial plateau 114. From there, the handle 14 may be rotated relative to the guide arm 12 (e.g., the angular rotation 21 depicted with reference to FIGS. 5A and 5B); and the handle 14 may be extended away from the guide arm 12 in an arcuate fashion (e.g., the path 19 depicted with reference to FIGS. 3A-3D). Such movement may position the sleeve 20 in the appropriate position as shown, at which point the position of the handle 14 (and thus the sleeve 20) relative to the guide arm 12 may be locked in place by manipulating the hinge 32 (e.g., along the path 33 depicted with reference to FIG. 7A-7E).

This method allows the camera 50 to capture one or more images of the tibial plateau 114 via the anteromedial portal 136 of the knee 110. Advantageously, by configuring the guide arm 12 to be advanced into the anterolateral portal 138, the camera 50 may then have a clear path shown (via the anteromedial portal 136) to view the tibial plateau 114 during a surgical procedure.

In further embodiments, and as shown with reference to FIG. 11B, the apparatus 10 may be configured such that the guide arm 12 may rather be advanced into the anteromedial portal 136, and thus the camera 50 may have a clear path shown via the anterolateral portal 138 to view the tibial plateau during a surgical procedure.

Figure 12:
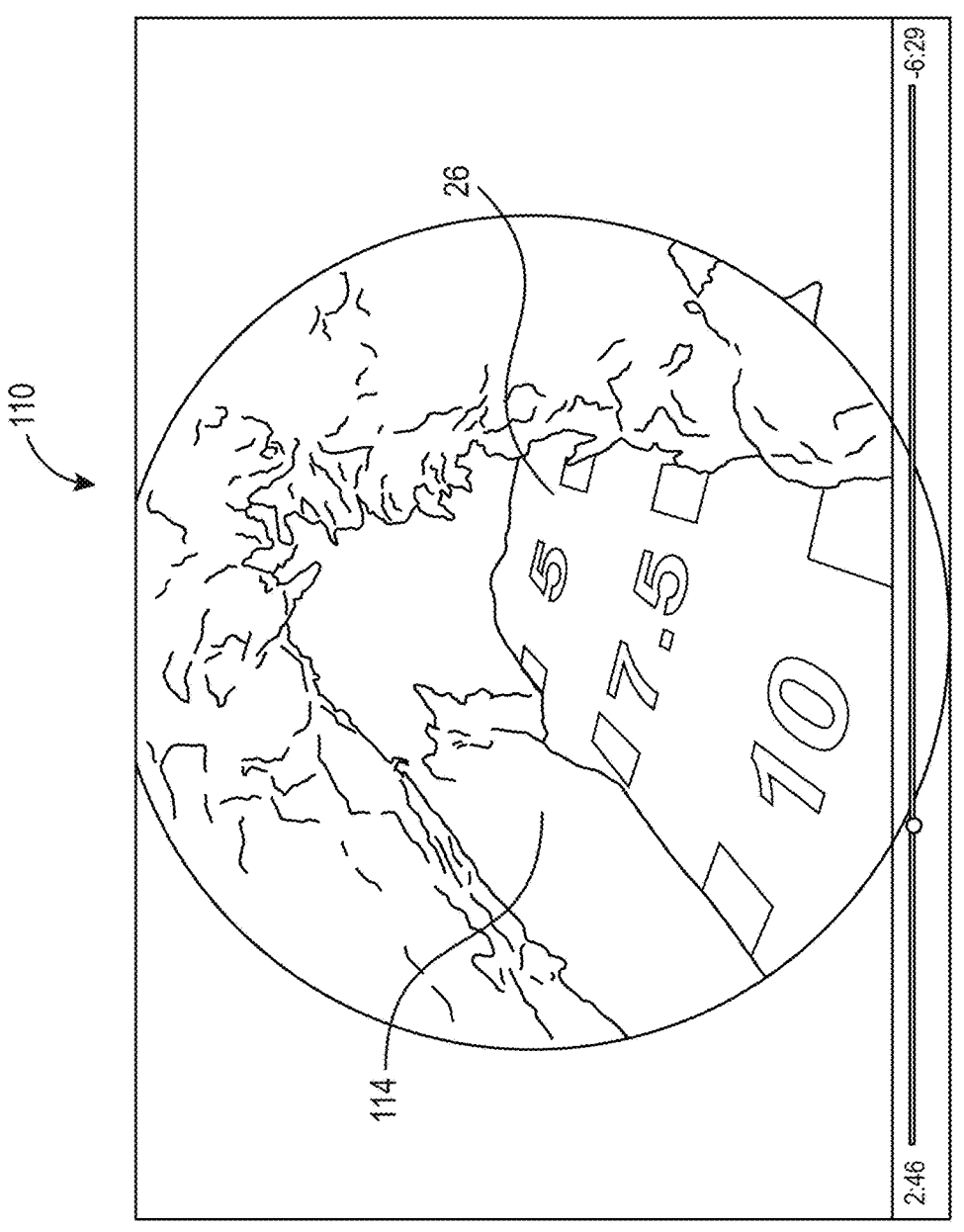
FIG. 12 is a camera view of a conventional approach where a camera views a tibial plateau via an anterolateral portal while a guide arm is introduced to the tibial plateau via an anteromedial portal.
Figure 13:
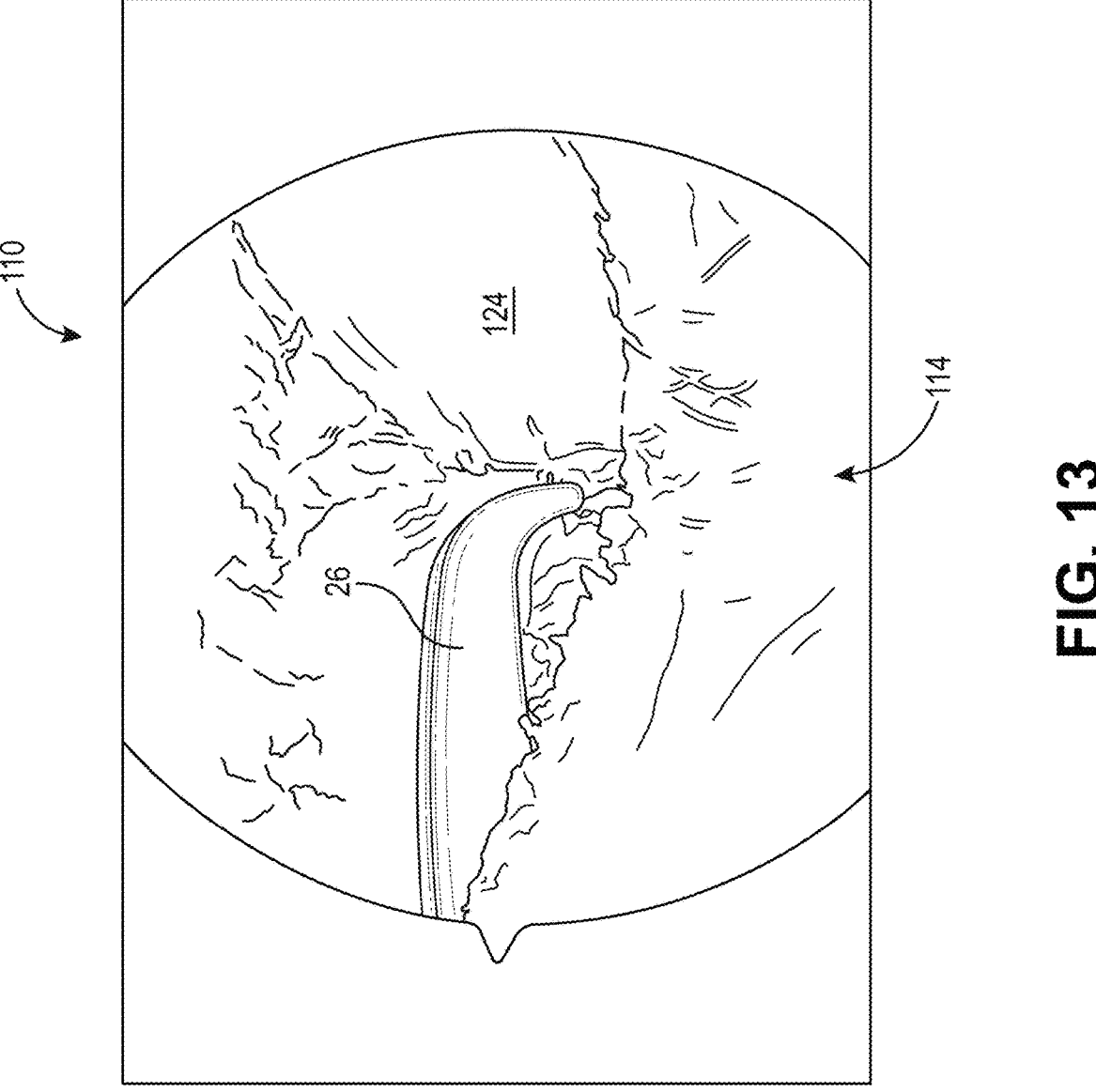
FIG. 13 is a camera view according to some embodiments of the present disclosure, where the camera has an improved view relative to FIG. 18 based on viewing the tibial plateau via the anteromedial portal while a guide arm is introduced to the tibial plateau via an anterolateral portal.
Figure 14:
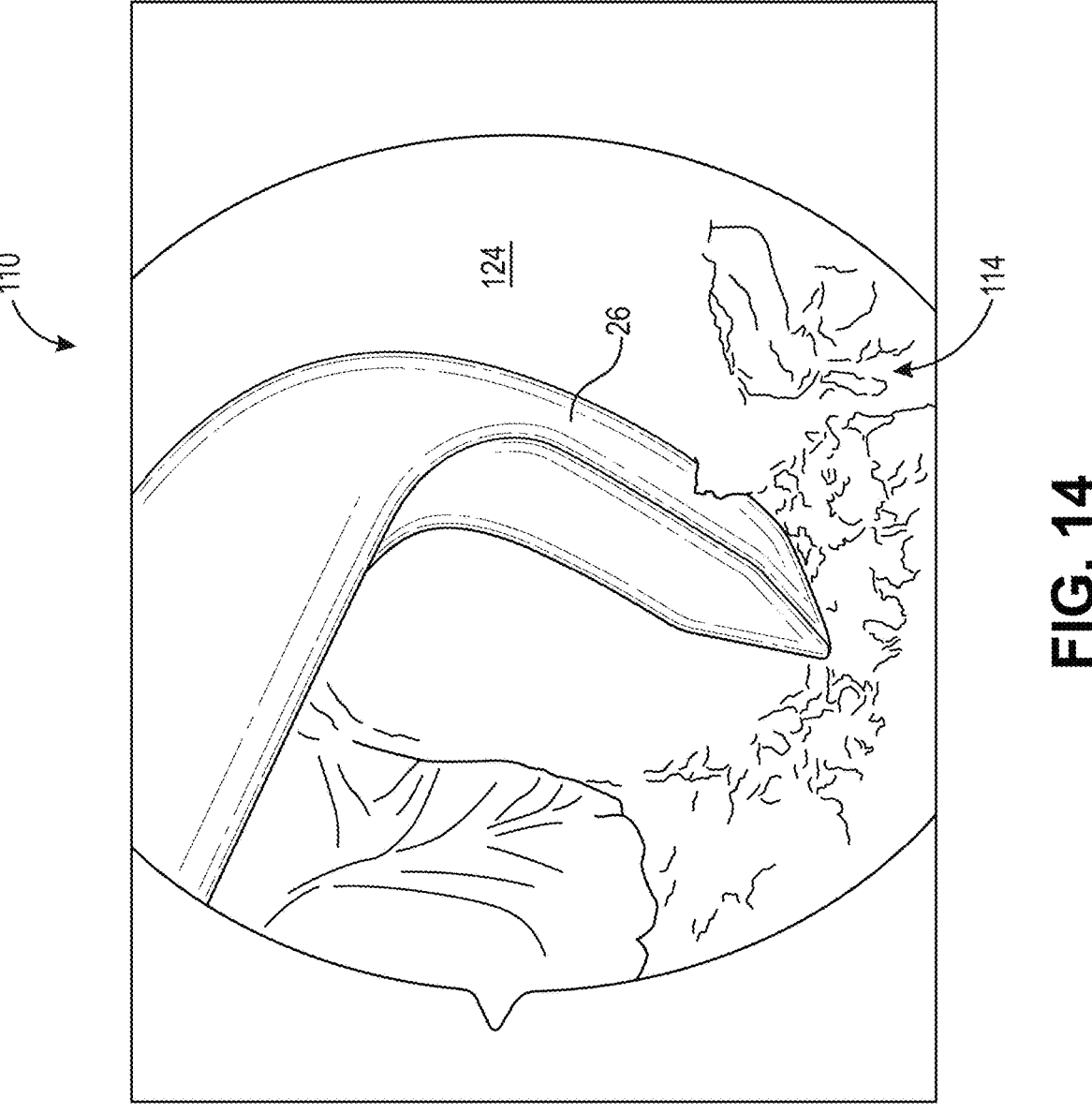
FIG. 14 is a camera view according to some embodiments of the present disclosure, where the camera has an improved view relative to FIG. 18 based on viewing the tibial plateau via the anteromedial portal while a guide arm is introduced to the tibial plateau via an anterolateral portal.

In order to illustrate an advantage of the apparatuses and methods discussed herein, FIG. 12 depicts a view of a camera viewing the tibial plateau through the anterolateral portal 138 of the knee 110 when the guide arm 12 has been introduced via the anteromedial portal 136. This may result in obliteration of the visual field for the camera since the tip 26 is covering over the meniscal root footprint. When the meniscal root footprint is covered by the guide arm 12, the user may have a difficult time performing surgery on the knee 110. Conversely, FIGS. 13 and 14 show the view of the camera 50 when the guide arm 12 is advanced into the anterolateral portal 138 and the camera 50 using the clear path through the anteromedial portal 136, as discussed herein. Advantageously, the view of the camera 50 is shown to be improved relative to the conventional method depicted with reference to FIG. 12. The tibial plateau 114 (the meniscal root, in particular) can be easily viewed using the apparatuses and methods discussed herein, and thus the tip 26 can be placed appropriately on the tibial plateau 114 (the meniscal root footprint, in particular), with reduced difficulty for the user.

Accordingly, an exemplary method of using the apparatus 10 as discussed herein may include advancing the guide 12 arm through the anterolateral portal 138 of the knee 110 and positioning the tip 26 on the tibial plateau 114 of the knee 110. The method may further include capturing, via the camera 50, one or more images of the tibial plateau 114 via the anteromedial portal 136 of the knee 110.

Referring again to FIGS. 3A-3D, the apparatus 10 is shown being extended as discussed above. Accordingly, after the tip 26 has been engaged with the tibial plateau 114 of the knee 110 as mentioned above with reference to FIG. 11, and before or after the guide arm 12 has been rotated relative to the handle 14, the neck 24 may be axially translated relative to the first handle passage 15 in order to suitably position the second handle passage 18 for guiding the sleeve 20 towards the tibia 112 of the knee. Thus, the aforementioned method of using the apparatus 10 may further include drawing the handle 14 away from the guide arm 12, such that the neck 24 is arcuately moved (e.g., axially moved considering the corresponding arcuate configurations) in translation relative to the first handle passage 15.

Referring again to FIGS. 5A and 5B, the apparatus 10 is shown the guide arm 12 being rotated relative to the handle 14. As shown and as discussed above, the handle 14 may be rotated relative to the guide arm 12 (via the lever 30 and as controlled by the detent mechanism 34) as appropriate for positioning the second handle passage 18 (and thus the sleeve 20) relative to the tibia 112 for proving a bone passage within the tibia 112 during surgery. Thus, the aforementioned method of using the apparatus 10 may further include rotating the lever 30 such that the guide arm 12 is angularly moved in rotation relative to the cuff 16.

Referring again to FIGS. 7A-7G, the apparatus 10 is shown with the lock mechanism securing the neck 24 in place relative to the handle 14. As discussed above, this may include, after positioning the second handle passage 18 appropriately, the hinge 32 being rotated between a first hinge position where the neck locking mechanism 31 holds the neck 24 in place relative to the first handle passage 15, and a second hinge position where the neck locking mechanism 31 releases the neck 24. Thus, the second handle passage 18 may be secured in place for advancement of the sleeve 20 towards the tibia 112. Accordingly, the aforementioned method of using the apparatus 10 may further include rotating the hinge 32, such that the neck locking mechanism 31 secures the neck 24 in place relative to the first handle passage 15.

Referring again to FIG. 11, the apparatus 10 is shown with the sleeve 20 being advanced into the tibia 112 for forming a bone passage during surgery on the knee 110. As discussed above, this may further incorporate the use of the sleeve locking mechanism 40, which may prevent the sleeve 20 from inadvertently retreating from the tibia 112 due to kick-back that may occur during the drilling process. In this sense, when the sleeve 20 is advanced through the second handle passage 18, the locking member 42 may be moved to a first driving member position where the sleeve 20 is axially movable in translation relative to the through-hole 46 from a second driving member position where the locking member 42 secures the sleeve 20 in place relative to the through-hole 46. The locking member 42 may be urged by the biasing member 44 towards the second driving member position. Accordingly, the aforementioned method of using the apparatus 10 may further include advancing the sleeve 20 through the second handle passage 18 and towards the knee 110 in order to provide the bone passage through the tibia 112.

Thus, although there have been described particular embodiments of the present invention of a new and useful SURGICAL DRILL GUIDE APPARATUS AND METHODS, it is not intended that such references to particular embodiments be construed as limitations upon the scope of this invention.

What is claimed is:

1. An apparatus for positioning and guiding a drill for forming a bone passage during surgery, the apparatus comprising: a handle; a sleeve disposed on the handle, the sleeve configured to receive a drill; a neck disposed on the handle and movable in translation relative to the handle; a lever disposed on the neck and angularly movable in rotation at least forty-five degrees in either direction relative to the neck; a guide arm disposed on the lever; a detent mechanism configured to provide a resistance against the rotation of the lever; and a neck locking mechanism disposed on the handle, the neck locking mechanism configured to hold the neck in place relative to the handle and release the neck.

2. The apparatus of claim 1, wherein the handle includes a first handle passage defined therein and a second handle passage defined therein, wherein the neck is disposed in the first handle passage, and wherein the sleeve is disposed in the second handle passage.

3. The apparatus of claim 2, wherein the neck includes a first end free of the first handle passage and a second end disposed in the first handle passage, wherein the neck includes a cuff defined on the first end, wherein the guide arm is disposed in the cuff, and wherein the guide arm is configured to be angularly movable in rotation relative to the cuff in response to the rotation of the lever.

4. The apparatus of claim 3, wherein the detent mechanism includes a plurality of ribs and a detent arm configured to mechanically engage one or more of the plurality of ribs.

5. The apparatus of claim 4, wherein the plurality of ribs are defined on the cuff, and wherein the detent arm is defined on the lever.

6. The apparatus of claim 1, wherein the neck locking mechanism includes a hinge, a cam and a shim, wherein the hinge is angularly movable in rotation relative to the handle, wherein the cam is angularly movable in rotation relative to the handle in response to the rotation of the hinge, wherein the shim is angularly movable in rotation relative to the handle in response to the rotation of the cam, wherein the cam is angularly movable in rotation relative to the handle, and wherein the rotation of the shim causes the shim to engage the neck and hold the neck in place relative to the handle.

7. The apparatus of claim 6, wherein the hinge is configured to be rotated by an index finger of a user.

8. The apparatus of claim 1, wherein the guide arm is configured to be engaged with a tibial plateau of a knee via an anteromedial portal of the knee.

9. The apparatus of claim 1, wherein the guide arm is configured to be engaged with a tibial plateau of a knee via an anterolateral portal of the knee.

10. The apparatus of claim 1, wherein the neck and the handle feature corresponding arcuate shapes.

11. The apparatus of claim 1, wherein the handle is configured to be gripped in a hand of a user, and the lever is configured to be rotated by a thumb of the user.

12. An apparatus for positioning and guiding a drill for forming a bone passage during surgery, the apparatus comprising:

a handle;

a sleeve disposed on the handle, the sleeve configured to receive a drill;

a neck disposed on the handle and movable in translation relative to the handle along an arcuate axis;

a lever disposed on the neck above the arcuate axis, the lever angularly movable in rotation relative to the neck;

a guide arm disposed on the lever, the guide arm extending below the handle; and a neck locking mechanism disposed on the handle, the neck locking mechanism configured to hold the neck in place relative to the handle and release the neck, wherein the neck locking mechanism includes a hinge disposed below the arcuate axis opposite the lever.

13. The apparatus of claim 12, wherein the hinge is angularly movable relative to the handle.

14. The apparatus of claim 13, wherein the neck locking mechanism further includes a shim that is angularly movable in rotation relative to the handle in response to rotation of the hinge, and wherein rotation of the shim causes the shim to engage the neck and hold the neck in place relative to the handle.

15. The apparatus of claim 14, wherein the neck locking mechanism further includes a cam that is angularly movable in rotation relative to the handle in response to rotation of the hinge.

16. The apparatus of claim 15, wherein the hinge is configured to be rotated by an index finger of a user.

17. The apparatus of claim 16, wherein the handle is configured to be gripped in a hand of a user, and the lever is configured to be rotated by a thumb of the user.

18. The apparatus of claim 17, further comprising a detent mechanism configured to provide a resistance against the rotation of the lever, wherein the handle includes a first handle passage defined therein and a second handle passage defined therein, wherein the neck is disposed in the first handle passage, wherein the sleeve is disposed in the second handle passage, wherein the neck includes a first end free of the first handle passage and a second end disposed in the first handle passage, wherein the neck includes a cuff defined on the first end, wherein the guide arm is disposed in the cuff, and wherein the guide arm is configured to be angularly movable in rotation relative to the cuff in response to the rotation of the lever.

19. The apparatus of claim 18, wherein the detent mechanism includes a plurality of ribs and a detent arm configured to mechanically engage one or more of the plurality of ribs, wherein the plurality of ribs are defined on the cuff, and wherein the detent arm is defined on the lever.

* * * * *